United States Patent [19]
Chester et al.

[11] Patent Number: 5,876,691
[45] Date of Patent: Mar. 2, 1999

[54] ANTIBODY AGAINST CARCIONEMBRYONIC ANTIGEN (CEA)

[75] Inventors: Kerry Anne Chester, London; Robert Edward Hawkins, Cambridge; Richard Henry John Begent, London, all of United Kingdom

[73] Assignee: Cancer Research Campaign Technology Limited, United Kingdom

[21] Appl. No.: 652,507

[22] PCT Filed: Dec. 5, 1994

[86] PCT No.: PCT/GB94/02658

§ 371 Date: Jul. 2, 1996

§ 102(e) Date: Jul. 2, 1996

[87] PCT Pub. No.: WO95/15341

PCT Pub. Date: Jun. 8, 1995

[30] Foreign Application Priority Data

Dec. 3, 1993 [GB] United Kingdom .................. 9324807

[51] Int. Cl.$^6$ ........................ A61K 51/00; A61K 39/395; C07K 16/00; C12Q 1/68
[52] U.S. Cl. .................. 424/1.49; 530/387.1; 530/387.3; 530/387.7; 530/388.1; 530/388.2; 530/388.8; 530/388.85; 530/391.1; 530/391.3; 530/391.7; 530/413; 530/130.1; 435/6; 424/178.1; 424/181.1
[58] Field of Search .............................. 530/387.3, 387.1, 530/387.7, 388.1, 388.2, 388.8, 388.85, 391.1, 391.3, 391.7; 435/7.1, 6; 424/130.1, 1.49, 178.1, 181.1

[56] References Cited

FOREIGN PATENT DOCUMENTS

| | | |
|---|---|---|
| A-11251/92 | 1/1993 | Australia . |
| 2107513 | 4/1994 | Canada . |
| 0 396 387 | 11/1990 | European Pat. Off. . |
| 0 497 585 A2 | 8/1992 | European Pat. Off. . |
| 0 501 215 A2 | 9/1992 | European Pat. Off. . |
| 0 590 530 A2 | 4/1994 | European Pat. Off. . |
| WO 88/07378 | 10/1988 | WIPO . |
| WO 91/01990 | 2/1991 | WIPO . |
| WO 92/01059 | 1/1992 | WIPO . |
| WO 92/15333 | 9/1992 | WIPO . |
| WO 93/03151 | 2/1993 | WIPO . |
| WO 94/19466 | 9/1994 | WIPO . |

OTHER PUBLICATIONS

Burgess et al. (J. Cell Bio. 111:2129–2138), 1990.
Lazar et al., (Mol. & Cell Biol. 8:1247–1252), 1988.
Tao et al., ( J. Immunol. 143:2595–2601), 1989.
Bowie et al., (Science, 247:1306–1310), 1990.
Osband, M. E. et al., 1990. Immunol. Today 11: 193–195.
Drewomlp. B. et al. 1986, Cancer Res. 46(10);5137–5143.
Bagshawe, K. D. 1991, Antibody Immunoconjugates and Radiopharmaceuticals 4(4):915–922.
Milenic, D. E. et al., 1991. Cancer Res. 51(23): 6363–6371.
Bosslet, K. et al., 1991. Br. J. Cancer, 63: 681–686.
Clackson et al Letters to Nature vol. 352 Aug. 1991 624–628 Making antibody fragments using phage display libraries.
Nap et al Cancer Research 52, 2329–2339, Apr. 1992 Specificity and Affinity of Monoclonal Antibodies against Carcinoembryonic Antigen.
Chester et al J. Cellular Biochem 1994 S18D 198 Production of a High Affinity Anti–Cea etc.
Chester et al The Lancet vol. 343 No. 8895 pp. 455–456 Feb. 1994 Phage libraries for generation of clinically useful antibodies. Date Considered.
Milstein et al Nature vol. 349 Jan. 1991 pp. 293–299 Man–made antibodies.
Goldenberg International J. of Biological Markers vol. 7 No. 3, pp. 183–188 Cancer imaging with CEA antibodies:historical and current perspectives, (1992).
Pedley et al (1993) Br. J. Cancer 68 pp. 69–73 Comparative radioimmunotherapy using intact or F(ab')$_2$ fragments of $^{131}$I anti–CEA antibody in a colonic xenograft model.
Pedley et al Int. J. Cancer 43, 713–718 (1989) The Effect of Second Antibody Clearance on the Distribution and Dosimetry of Radiolabelled Anti–CEA Antibody in a Human Colonic tumor Xenograft Model.
Ledermann et al 1988 Br. J. Cancer 58 654–659 Repeated Antitumour antibody therapy in man with suppression of the host response by Cyclosporin A.
Lederman et al Int. J. Cancer 47, 659–664 (1991) A Phase–I study of repeated therapy with radiolabelled antibody to carcinoembryonic antigen using intermittent or contnuous administration of cyclosporin A etc.
Boxer et al Br. J. Cancer (1992), 65, 825–831 Factors influencing variability of localisation of antibodies etc.

*Primary Examiner*—Lila Feisee
*Assistant Examiner*—Susan Ungar
*Attorney, Agent, or Firm*—Nixon & Vanderhye

[57] ABSTRACT

The invention provides an antibody specific for carcinoembryonic antigen (CEA) which has a dissociation constant (Kd; of less than 5.0 nM for said antigen. The antibody is generally a single chain Fv (scFv) antibody. The antibody was initially obtained by screening a bacteriophage library for phage expressing high affinity CEA antibody. The antibody is useful for diagnosis and therapeutic treatment of colorectal tumors.

23 Claims, 9 Drawing Sheets

Fig.3A.

810 b.p.    GAGACAGTCATA ... AAACGGGCGGCC    linear

```
1/1                                                                31/11
GAC ACA GTC ATA ATG AAA TAC CTA TTg ccT acG GCA GCC GCT GGA TTG TTA TTA CTC GCG
glu thr val ile met lys tyr leu leu pro thr ala ala gly leu leu leu leu ala
61/21                                                              91/31
GCC CAG CCG GCC atg GCC CAG GTG AAA CTG CAG TCT GGG GCA GAA CTT GTG AGG TCA
ala gln pro ala met ala gln val lys leu gln ser gly ala glu leu val arg ser
121/41                                                             151/51
GGG ACC TCA GTC AAG TTG TCC TGC ACA GCT TCT GGC TTC AAC ATT AAA GAC TCC TAT ATG
gly thr ser val lys leu ser cys thr ala ser gly phe asn ile lys asp ser tyr met
181/61                                                             211/71
CAC TGG TTG AGG CAG CCT GAA CAG GGC CTG GAG TGG ATT GGA TGG ATT GAT CCT GAG
his trp leu arg gln pro glu gln gly leu glu trp ile gly trp ile asp pro glu
241/81                                                             271/91
AAT GGT GAT ACT GAA TAT GCC CCG AAG TTC CAG GGC AAG GCC ACT TTT ACA GAC ACA
asn gly asp thr glu tyr ala pro lys phe gln gly lys ala thr phe thr asp thr
301/101                                                            331/111
TCC TCC AAC ACA GCC TAC CTG CAG CTC AGC AGC CTG ACA TCT GAG GAC ACT GCC TAT
ser ser asn thr ala tyr leu gln leu ser ser leu thr ser glu asp thr ala tyr
361/121                                                            391/131
TAT TGT AAT GAG GGG CCG ACT CCG GGG CCG TAC TAC TTT GAC TAC TGG GGC CAA GGG ACC
tyr cys asn glu gly pro thr pro gly pro tyr tyr phe asp tyr trp gly gln gly thr
```

Fig.3B.

```
421/141
ACG GTC ACC GTC TCC TCA GGT GGA GGC GGT     TCA GGT GGA GGC GGT
thr val thr val ser ser gly gly gly gly     451/151
481/161                                      TCA GGC TCA GGT GGC GGA GGT GGC TCT GGC GGT GGC GGA
TCA GaA AAT GTG CTC ACC CAG TCT CCA GCA     ser gly ser gly gly gly gly ser gly gly gly gly
ser glu asn val leu thr gln ser pro ala     511/171
541/181                                      TCT GCA TCT CCA GGG GAG AAG GTC
ACC ATA ACC TGC AGT GCC AGC TCA AGT GTA     ser ala ser pro gly glu lys val
thr ile thr cys ser ala ser ser val          571/191
601/201                                      ATG CAC TGG TTC CAG CAG AAG CCA
GGC ACT TCT CCC AAA CTC TGG ATT TAT          met his trp phe gln gln lys pro
gly thr ser pro lys leu trp ile tyr          631/211
661/221                                      AAC TCC GCT TCT GGA GTC CCT GCT
CGC TTC AGT GGA TCT GGA TCT GGG ACC TCT      asn ser ala ser gly val pro ala
arg phe ser gly ser gly ser gly thr ser      691/231
721/241                                      TAC TCT ACA ATC AGC CGA ATG GAG GCT
GAA GAT GCT GCC ACT TAT TAC TGC CAG CAA      leu thr ile ser arg met glu ala
glu asp ala ala thr tyr tyr cys gln gln      751/251
781/261                                      AGT AGT TAC CCA CTC ACG TTC GGT GCT
GGC ACC AAG CTG GAG CTG AAA CGG GCG GCC      ser ser tyr pro leu thr phe gly ala
gly thr lys leu glu leu lys arg ala ala
```

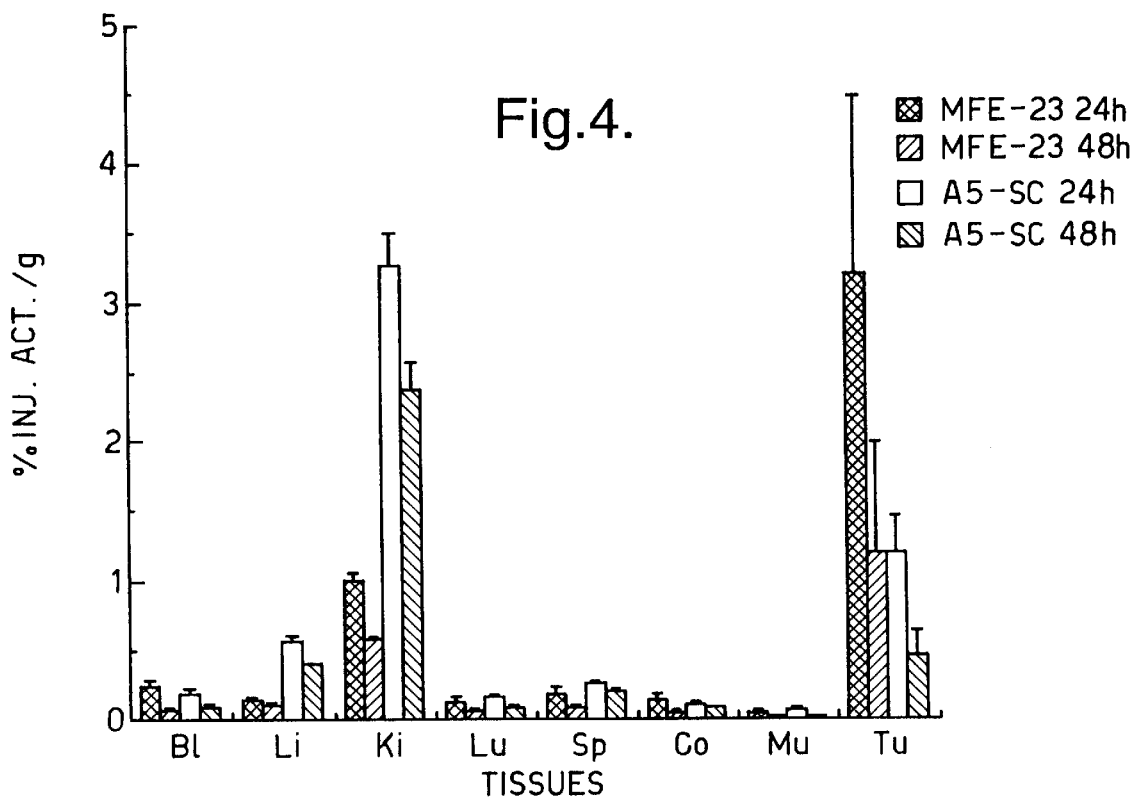
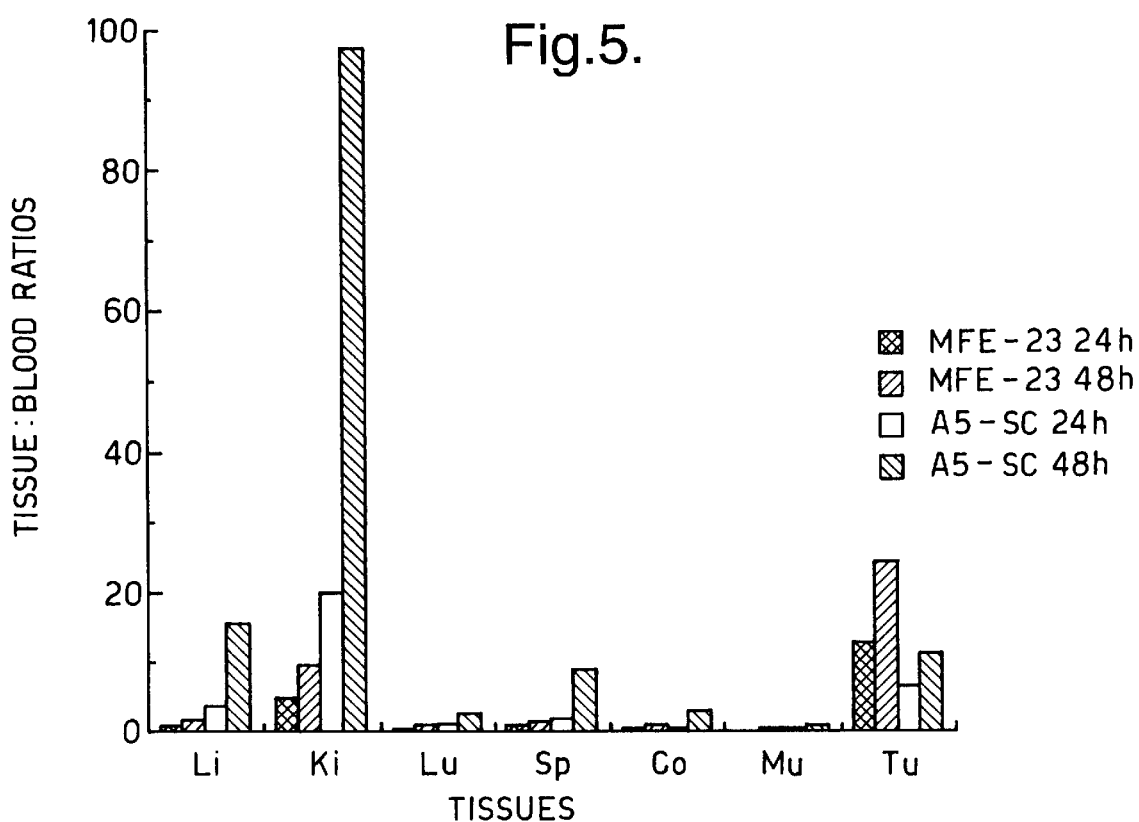

Fig. 6.

pSNCH6 - Vector for purification and labelling

Hind III
<u>aag ctt</u> gca tgc aaa ttc tat ttc aag gag aca gtc ata atg aaa tac cta ttg cct acg
                                                                      M   K   Y   L   L   P   T
                                                                       PEL B leader Sfi I          Nco I
gca gcc gct gga ttg tta ctc gcg <u>gcc cag ccg</u> <u>gcc</u> atg gcc cag gtg cag ctg cag
 A   A   A   G   L   L   L   A   A   Q   P   A   M   A   Q   V   Q   L   Q
  PEL B leader Not I                                                    Eco RI
gtc ggc ctc gag atc aaa cgg <u>gcg gcc gca</u> tgt cat cac cat cac cat taa taa <u>gaa ttc</u>
 V   G   L   E   I   K   R   A   A   A   C   H   H   H   H   H   *   *
                                                       TAG for purification/labelling

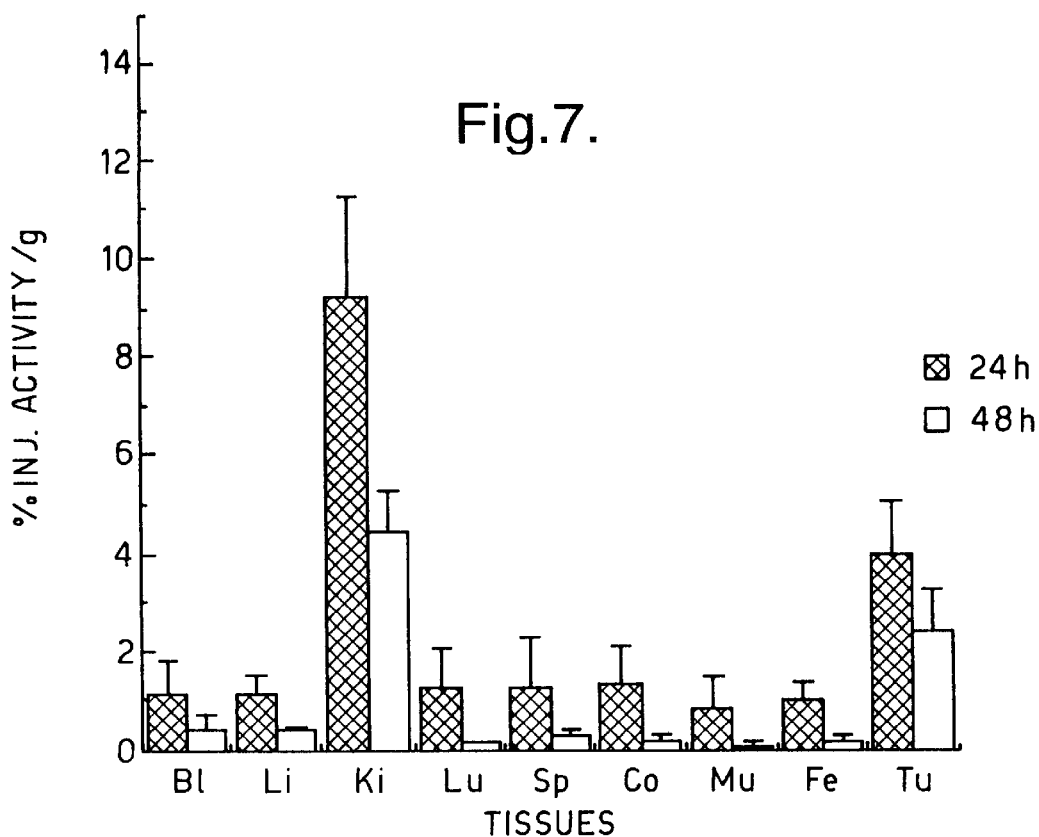
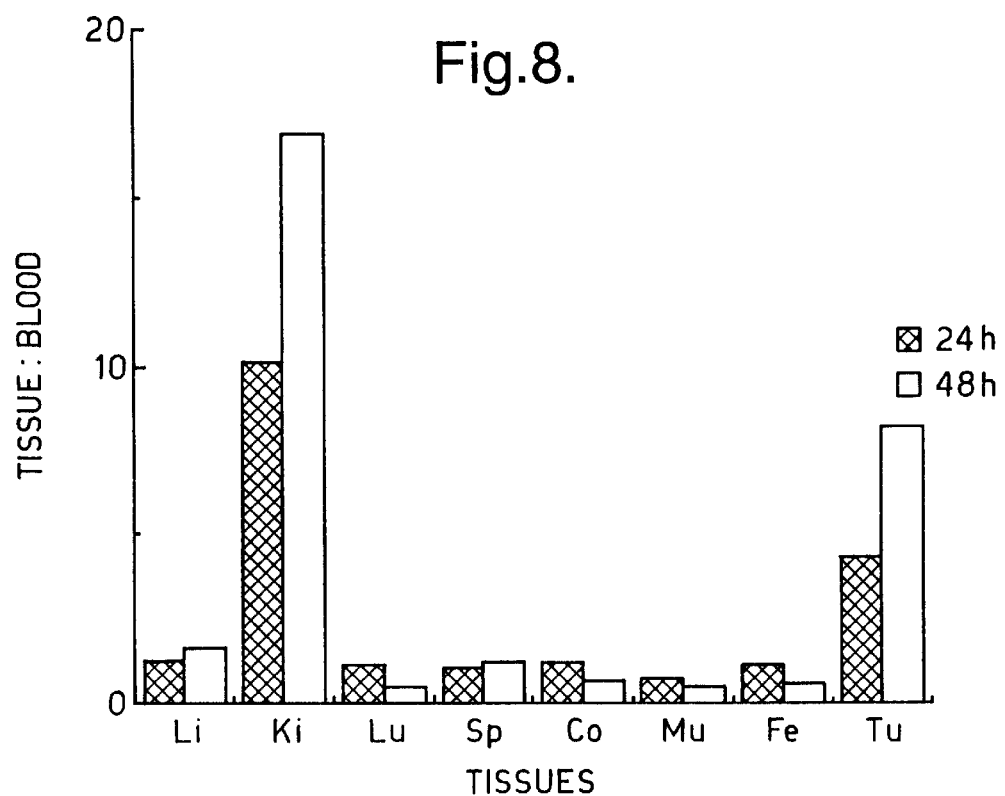

HIS TAG...

```
            H  H  H  H  H  H  *  *
VL.......CATCACCATCATCACCATTAATAA
```

ANTIBODY AGAINST CARCIONEMBRYONIC ANTIGEN (CEA)

The present invention relates to antibodies against carcinoembryonic antigen (CEA) and their use in diagnosis and therapy.

CEA is an antigen which is expressed on tumours such as colorectal tumours and is therefore a marker for tumour cells. Various tumour cell markers are known in the art and it has been proposed that therapy against these tumours can be achieved by targeting agents against these markers. Usually, the agent is an antibody or fragment thereof which has been linked to a cytotoxic agent or to an enzyme capable of converting a pro-drug into an active cytotoxic agent.

Alternatively, the antibodies can be linked to imaging agents. This is useful in the diagnosis and prognosis of conditions which involve the expression of a tumour cell marker.

The use of cell surface markers as target agents has been reviewed by Begent, 1990 (see ref 1 below).

There are two main criteria to consider when selecting an antibody suitable for use in targeted anti-tumour therapies. It is desirable that the antibody has a good affinity for its target antigen. This is required so that once the antibody has reached its target, it remains bound to that target for long enough to achieve the desired result, for example cytotoxicity.

In addition, the antibody should have good specificity for the target antigen so that binding to non-target antigens does not occur to any significant extent.

Many antibodies are produced on a commercial scale by recombinant means. This usually involves expression of the antibody in a host cell such as *E.coli* or yeast. It is therefore desirable that the antibody is encoded by a s nucleic acid sequence which is capable of high levels of expression in a host cell. For reasons that are still not well understood some recombinant nucleic acid sequences can be expressed less well than others by particular types of cells.

CEA has been used as a marker antigen for cancer imaging (ref 8) and therapy (refs 9–13). A large number of CEA antibodies with different specificities and affinities are known (ref 7). One antibody which is widely used in the art against CEA is A5B7. This antibody is useful in imaging and therapy, and has been used in human trials (refs 9, 12, 13). Although many antibodies to CEA exist, the A5B7 antibody has to date been considered the most promising.

We have now found that it is possible to obtain antibody of good specificity and considerably greater affinity to CEA that A5B7 (about 10 times greater affinity). The antibody has proved superior in tumour localisation in vivo to A5B7, and a higher proportion and amount of the antibody is localised to tumour rather than to other body tissues. A clinical trial of tumour imaging with the antibody has begun with successful tumour localisation in 8 patients with colorectal carcinoma. No non-specific antibody localisation was seen.

The antibody was initially obtained from a bacteriophage library. Antibody genes were inserted into bacteriophage and the resulting library of $10^7$ phage was screened for expression of antibody against CEA. Genes encoding the desired antibody were selected and the genes were expressed in bacteria.

In a first embodiment, the invention provides an antibody specific for CEA which has a dissociation constant (Kd) of less than 5.0 nM. The antibody generally has a dissociation constant of from 0.5 to 5.0 nM, for example a dissociation constant of 2.5+/−1.3 nM. Preferably the antibody will bind competitively for the epitope on CEA recognised by the MFE-23 antibody described below.

The specificity of the antibody is preferably such that it binds to human colorectal adenocarcinoma but does not bind to some or all of the following normal tissues: liver, kidney, large intestine, tonsil, lung, brain, testis, ovary, cervix, breast, blood films, placenta, spleen, thyroid, oesophagus, stomach, pancreas, lymph node and skeletal muscle. This is in contrast to many CEA antibodies which commonly show cross reaction with a variety of normal tissues (see ref 7).

The term "antibody" is used herein to include complete antibodies (i.e. antibodies having two heavy and two light chains) as well as fragments of antibodies which contain an antigen binding site, such as Fab, F(ab')$_2$, Fv and single chain Fv (scFv) fragments. However, the antibody according to the invention is preferably an scFv antibody. scFvs are composed of an antibody variable light chain (VL) linked to a variable heavy chain (VH) by a flexible linker. scFvs are able to bind antigen and can be rapidly produced in bacteria. It has also now been found that scFvs exhibit superior tumour localisation and therefore offer advantages for in vivo use.

A particularly preferred antibody according to the invention is the MFE-23 antibody shown in FIG. 3 (SEQ ID No. 2). The sequence of MFE-23 may be used to design other antibodies of similar specificity. In particular, the sequence may be used to design antibodies having the complementarity determining regions (CDRs) of MFE-23. These regions are shown at the following locations in FIG. 3 (SEQ ID No: 2) : Gly 52 to His 61, Trp 76 to Glu 85, Gly 125 to Tyr 135, Ser 185 to His 194, Ser 210 to Ser 216 and Gln 249 to Thr 257. The sequence of MFE-23 may also be used to design an antibody having a VH chain region of the sequence from Gln 27 to Ser 146 of FIG. 3 (SEQ ID No: 2) and a VL chain region of the sequence from Glu 162 to Lys 267 of FIG. 3 (SEQ ID No: 2). It is also possible to make an antibody having a variable (V) region of the sequence from Gln 27 to Lys 267 of FIG. 3 (SEQ ID No: 2). A humanised antibody with CDRs of MFE-23 may be made, for example in accordance with the methods disclosed in EP-A-0239400 (Winter).

In addition, it is possible to design antibodies comprising CDR sequences which are at least 60% identical to the CDR sequences from FIG. 3 (SEQ ID No: 2) defined above. Such antibodies preferably comprise sequences at least 80%, more preferably at least 90% or even 95% identical to the sequences from FIG. 3 (SEQ ID No: 2). These antibodies must retain the high affinity and specificity for CEA of the antibodies containing sequences identical to sequences from FIG. 3 (SEQ ID No: 2). In general, the physiochemical nature of the sequences from FIG. 3 should be preserved in the antibodies containing modified sequences. The amino acids in the modified sequences should generally be similar in charge, hydrophobicity/hydrophilicity and size. Candidate substitutions are those in which an amino acid from one of the following groups is replaced by a different amino acid from the same group:

H, R and K
I, L, V and M
A, G, S and T
D, E, P and N

Further, the sequence of MFE-23 may be used to make diabodies, i.e. bivalent or bispecific antibody fragments which bind to two different antigens. For example, a diabody bispecific for CEA and CD16 has been constructed from MFE-23 and anti-CD16 antibody V genes derived from hybridoma 3G8 (ref 25). Such diabodies promise to be powerful reagents to target cell destruction utilising natural cellular effector mechanisms.

The antibody according to the invention may be linked to an antitumour agent or a detectable label. This allows the antibody to target the antitumour agent or detectable label to the tumour and hence allows damage/destruction or detection of the tumour. Thus, the antibody is suitable for use in a method of treatment of the human or animal body by therapy or surgery (e.g. radioimmunoguided surgery), or in a method of diagnosis practised on the human or animal body. In particular, the antibody is suitable for use in treatment by surgery or therapy of a colorectal tumour, or in diagnosis of a colorectal tumour. A review of use of antibodies in diagnosis and therapy is provided by ref 26.

The antitumour agent linked to the antibody may be any agent that destroys or damages a tumour to which the antibody has bound or in the environment of the cell to which the antibody has bound. For example, the antitumour agent may be a toxic agent such as a chemotherapeutic agent or a radioisotope, an enzyme which activates a prodrug or a cytokine.

Suitable chemotherapeutic agents are known to those skilled in the art and include anthracyclines (e.g. daunomycin and doxorubicin), methotrexate, vindesine, neocarzinostatin, cis-platinum, chlorambucil, cytosine arabinoside, 5-fluorouridine, melphalan, ricin and calicheamicin. The chemotherapeutic agents may be conjugated to the antibody using conventional methods (see e.g. ref 27).

Suitable radioisotopes for use as antitumour agents are also known to those skilled in the art. For example, $^{131}$I or astatine such as $^{211}$At may be used. These isotopes may be attached to the antibody using conventional techniques (see e.g. ref 11).

The antitumour agent which is attached to the antibody may also be an enzyme which activates a prodrug. This allows activation of an inactive prodrug to its active, cytotoxic form at the tumour site and is called "antibody-directed enzyme prodrug therapy" (ADEPT). In clinical practice, the antibody-enzyme conjugate is administered to the patient and allowed to localise in the region of the tumour to be treated. The prodrug is then administered to the patient so that conversion to the cytotoxic drug is localised in the region of the tumour to be treated under the influence of the localised enzyme.

A preferred enzyme is bacterial carboxypeptidase G2 (CPG2) whose use is described in, for example, WO 88/07378. A conjugate between an antibody according to the invention and CPG2 shows good tumour localisation. The antibody-enzyme conjugate may if desired be modified in accordance with the teaching of WO 89/00427, in order to accelerate clearance from areas of the body not in the vicinity of a tumour. The antibody-enzyme conjugate may also be used in accordance with WO 89/00427, for example, by providing an additional component which inactivates the enzyme in areas of the body not in the vicinity of the tumour.

The antitumour agent conjugated to the antibody may also be a cytokine such as interleukin-2 (IL-2), interleukin-4 (IL-4) or tumour necrosis factor alpha (TNF-α). The antibody targets the cytokine to the tumour so that the cytokine mediates damage to or destruction of the tumour without affecting other tissues. The cytokine may be fused to the antibody at the DNA level using conventional recombinant DNA techniques.

The detectable label attached to the antibody may be an imaging agent for tumour imaging such as a short-lived radioisotope, for example $^{111}$In, $^{125}$I or $^{99m}$Tc. A review of cancer imaging with CEA antibodies is provided by ref 8.

$^{99m}$Tc is a preferred imaging agent, mainly because it can be attached to an antibody at a position away from the antigen binding site and this gives improvements in tumour localisation. $^{99m}$Tc may be linked to the antibody by a free Cys residue provided at or near the N- or C-terminus of the antibody. An antibody having such a free Cys residue may be prepared by recombinant DNA techniques, for example by making a vector encoding the antibody-Cys fusion and expressing the antibody-Cys fusion in a host cell such as a bacterial host cell. The Cys residue is typically at the terminus of the antibody but may, for example, be the 2nd to 20th residue from the terminus.

An antibody according to the invention containing a detectable label is useful for radioimmunoguided surgery (RIGS, refs 30 and 31) in addition to being useful for diagnosis of tumours. RIGS comprises administering a labelled antibody to a patient and thereafter surgically removing any tissue to which the antibody binds. Thus, the labelled antibody guides the surgeon towards tumour tissue and helps to distinguish from normal tissue.

The antibody according to the invention may also be used for in vitro detection or quantitative determination of CEA. For example, the antibody may be used for enzyme-linked immunoassay (ELISA), Western blotting or in situ detection of CEA in a tissue sample. Thus, the antibody may be used in a method for detecting or quantitatively determining CEA in a sample, which method comprises (i) contacting the sample with a labelled antibody, and (ii) detecting or quantitatively determining labelled antibody bound to any CEA in the sample.

Typically, an ELISA method for detecting or quantitatively determining CEA in a sample using an antibody according the invention comprises (i) immobilising on a solid support an unlabelled antibody according to the invention, (ii) adding the sample such that any CEA in the sample is captured by the unlabelled antibody, (iii) adding a labelled antibody according to the invention, and (iv) detecting or quantitatively determining any bound labelled antibody.

An antibody of the invention may also be employed histologically for in situ detection or quantitative determination of CEA, for example by immunofluorescence or immunoelectron microscopy. In situ detection or determination may be accomplished by removing a tissue specimen from a patient and allowing a labelled antibody to bind to any CEA in the specimen. Through use of such a procedure, it is possible to find not only the presence f CEA but also its spatial distribution.

An antibody of the invention may be used to purify CEA. Conventional methods of purifying an antigen using an antibody may be used. Such methods include immunoprecipitation and immunoaffinity column methods. In an immunoaffinity column method, an antibody in accordance with the invention is coupled to the inert matrix of the column and a sample containing CEA is passed down the column, such that CEA is retained. The CEA is then eluted.

The sample containing CEA used in the above detection, determination and purification methods may be a tissue specimen or a cell extract from a patient. Alternatively, the sample may be one produced as a result of recombinant DNA procedures, e.g. an extract of a culture of host cells expressing CEA.

The detectable label attached to the antibody for in vitro use may be a radioisotope (e.g. $^{32}$p or 35S), biotin (which may be detected by avidin or steptavidin conjugated to peroxidase), digoxigenin, alkaline phosphatase or a fluorescent label (e.g. fluorescein or rhodamine).

The invention includes a DNA molecule encoding an antibody according to the invention. The DNA molecule may, for example, comprise the sequence shown in FIG. 3 (SEQ ID No: 1), or the VH chain coding region from nucleotide 79 to nucleotide 438 of FIG. 3 (SEQ ID No: 1) and the VL chain coding region from nucleotide 484 to nucleotide 801 of FIG. 3 (SEQ ID No: 1).

A further embodiment of the invention provides vectors for the replication and expression of DNA encoding an antibody according to the invention. The vectors may be, for example, plasmid, virus or phage vectors provided with an origin of replication, optionally a promoter for the expression of the said DNA and operably linked to said DNA. "Operably linked" refers to a juxtaposition wherein the promoter and the antibody coding sequence are in a relationship permitting the coding sequence to be expressed under the control of the promoter. The vector may also comprise a regulator of the promoter. The vector may contain one or more selectable marker genes, for example an ampicillin resistance gene in the case of a bacterial plasmid or a neomycin resistance gene for a mammalian vector. The vector may be used in vitro, for example for the production of RNA corresponding to the DNA, or used to transfect or transform a host cell.

The invention also provides host cells transformed or transfected with the vectors for the replication and expression of DNA encoding an antibody according to the invention. The cells will be chosen to be compatible with the vector and may for example be bacterial, yeast, insect or mammalian. Bacterial cells, particularly *E. coli* cells, are preferred because they allow high levels of antibody to the produced in soluble form. The invention includes a process for producing an antibody according to the invention, which process comprises (i) culturing a host cell as described above under conditions such that the antibody is expressed, and (ii) recovering the antibody from the culture.

Although this process is suitable for large scale production of an antibody according to the invention, it cannot of course be used to perform the initial isolation of the antibody. The initial isolation may be performed by screening a bacteriophage library for phage expressing CEA antibody. This system has been found to allow antibodies of greater affinity and higher specificity to be isolated. The isolation method generally comprises (i) selecting from a bacteriophage library a bacteriophage which expresses said antibody, (ii) infecting a bacterial host cell with the selected bacteriophage, (iii) culturing the host cell under conditions such that said antibody is expressed, and (iv) recovering said antibody from the culture.

The bacteriophage are generally filamentous bacteriophage. The bacterial host cell is generally an *E. coli* cell.

The bacteriophage library may be made by (a) immunizing an animal with CEA, (b) obtaining lymphocytes from the animal, (c) preparing cDNAs encoding antibody VH and VL regions from the mRNA of the lymphocytes, (d) joining VH and a VL coding regions by a sequence encoding a linker, and (e) inserting the joined regions into bacteriophage.

The animal immunised with CEA in step (a) is suitably a mouse, rat, rabbit or coat. In step (b), the lymphocytes are typically obtained from the spleen for the animal. It is usually necessary to amplify the cDNAs encoding VH and VL regions produced in step (c) before they are joined in step (d). The amplification may be carried out by polymerase chain reaction (PCR).

A method for purifying an antibody according to the invention to a level suitable for clinical use has been found. This method involves providing a His tag of at least three consecutive His residues at or near the N- or C-terminus of the antibody. The tag facilitates binding of the antibody to a solid support containing metal ions and hence allows the antibody to be separated from other components. Accordingly, the invention provides a method for purifying an antibody comprising a His tag from a biological liquid, which method comprises (i) contacting a solid support containing metal ions with the biological liquid under conditions such that the antibody binds to the support, (ii) removing biological liquid which is not bound to the support, and (iii) recovering the antibody from the support.

We have found that this method is superior to conventional methods for purifying antibodies such as immunoaffinity and ion-exchange chromatography. In particular; (1) a higher yield of antibody is produced, (2) scale-up is simple and cheap, and (3) the risk of tumour derived antigen leaching from the support is eliminated.

The length and position of the His tag in the antibody are chosen so as to optimise binding to metal ions without affecting antigen binding. The His tag may, for example, comprise from 3 to 20 His residues, preferably from 3 to 10 His residues, most preferably 5 or 6 His residues. The His residue at the end of the tag sequence closest to the terminus of the antibody is preferably the 15th or less, more preferably the 5th or less, amino acid from the terminus. The tag may be engineered into the antibody using recombinant DNA techniques.

The metal ions are generally transition metal ions, preferably transition metal ions carrying a 2+ charge such as $Ni^{2+}$, $Zn^{2+}$, and $Cu^{2+}$. $Cu^{2+}$ ions are preferred because they have been found to be highly effective in purifying the antibody.

The solid support is preferably the matrix of an affinity column (e.g. an iminodiacetic acid (IDA) column), although other supports such as beads may be used. When an affinity column is used, the biological liquid is loaded onto the column, unbound liquid is collected at the bottom, and bound antibody is then eluted from the column. When beads are used, the biological liquid is contacted with the beads, the beads are separated from unbound liquid, and bound antibody is recovered from the beads. The biological liquid is generally liquid from a culture of host cells (e.g. bacterial cells) expressing the antibody.

The invention includes a pharmaceutical composition comprising an antibody according to the invention having an antitumour agent or detectable label attached thereto and a pharmaceutically acceptable carrier or diluent. In clinical use, the antibody will normally be administered parenterally, e.g. intravenously or intraperitonealy. Thus, the pharmaceutical composition is normally one which is suitable for parenteral (e.g. intravenous or intraperitoneal) administration. Such a composition conveniently contains the antibody and isotonic saline or bicarbonate as diluent. The dose of antibody will ultimately be at the discretion of the physician, who will take account of factors such as the type of therapy or diagnosis and the weight, condition and age of the patient. Suitable doses of antibody are known in the art; see, for example, refs 9, 11, 13 and 29. A suitable dose may be from 0.01 to 100 mg, preferably from 0.1 to 10 mg for a human patient. The antibody according to the invention can be used in a similar way to known CEA antibodies (refs 8–13).

The following Examples illustrate the invention.

BRIEF DESCRIPTION OF THE DRAWINGS

FIGS. 3A and 3B show the sequence of antibody MFE23 and the corresponding nucleotide sequence. The antibody sequence is believed to start from about amino acid Gln 27. The locations of the CDRs, framework regions and linker are as follows:

| | |
|---|---|
| Framework H1: | Gln 27 to Ser 51 |
| CDR H1: | Gly 52 to His 61 |
| Framework H2: | Trp 62 to Gly 75 |
| CDR H2: | Trp 76 to Glu 85 |
| Framework H3: | Tyr 86 to Glu 124 |
| CDR H3: | Gly 125 to Tyr 135 |
| Framework H4: | Trp 136 to Ser 146 |
| Linker: | Gly 147 to Ser 161 |
| Framework Li: | Glu 162 to Cys 184 |
| CDR L1: | Ser 185 to His 194 |
| Framework L2: | Trp 195 to Tyr 209 |
| CDR L2: | Ser 210 to Ser 216 |
| Framework L3: | Gly 217 to Cys 248 |
| CDR L3: | Gln 249 to Thr 257 |
| Framework L4: | Phe 258 to Lys 267. |

FIGS. 4 and 5 show, in terms of injected activity per gram of tissue and tissue to blood ratios respectively, the biodistribution of antibodies MFE-23 and A5-SC after 24 h and 48 h in mice bearing human colorectal carcinoma xenografts. Antibody A5-SC is an scFv antibody derived from monoclonal antibody A5B7. With respect to the tissues tested, Li is liver, Ki is kidney, Lu is lung, Sp is spleen, Co is colon, Mu is muscle, Tu is tumour and Bl is blood.

FIG. 6 shows a pUC 119 construct used to clone MFE-cys. The vector contains a cysteine-histidine tag. The flexible linker consists of 15 amino acids (Gly 4 Ser)x3$^{23}$. The pelB signal sequence directs antibody fragments into the bacterial periplasm where they fold into antigen binding conformation$^{24}$. The nucleotide and amino acid sequences of FIG. 6 are SEQ ID Nos. 5 and 6 respectively.

FIG. 7 shows the localisation in the LS174T colon xenograft of $^{99m}$Tc-MFE-cys and I-125 MFE-23: Results are expressed as percent injected activity per gram of tissue at 24 and 48 h after injection. Blood (Bl), Liver (Li), Kidney (Ki), Lung (Lu), Spleen (Sp), Colon (Co), Muscle (Mu), Femur (Fe), and Tumour (Tu). 4 mice per group. Bars: SD.

FIG. 8 shows tissue to blood ratios of $^{99m}$Tc-MFE-cys in LS147T colon xenograft at 24 and 48 h after injection: Liver (Li), Lung (Lu), Spleen (Sp), Colon (Co), Muscle (Mu), Femur (Fe) and Tumour (Tu) . 4 mice per group.

Figure 9:
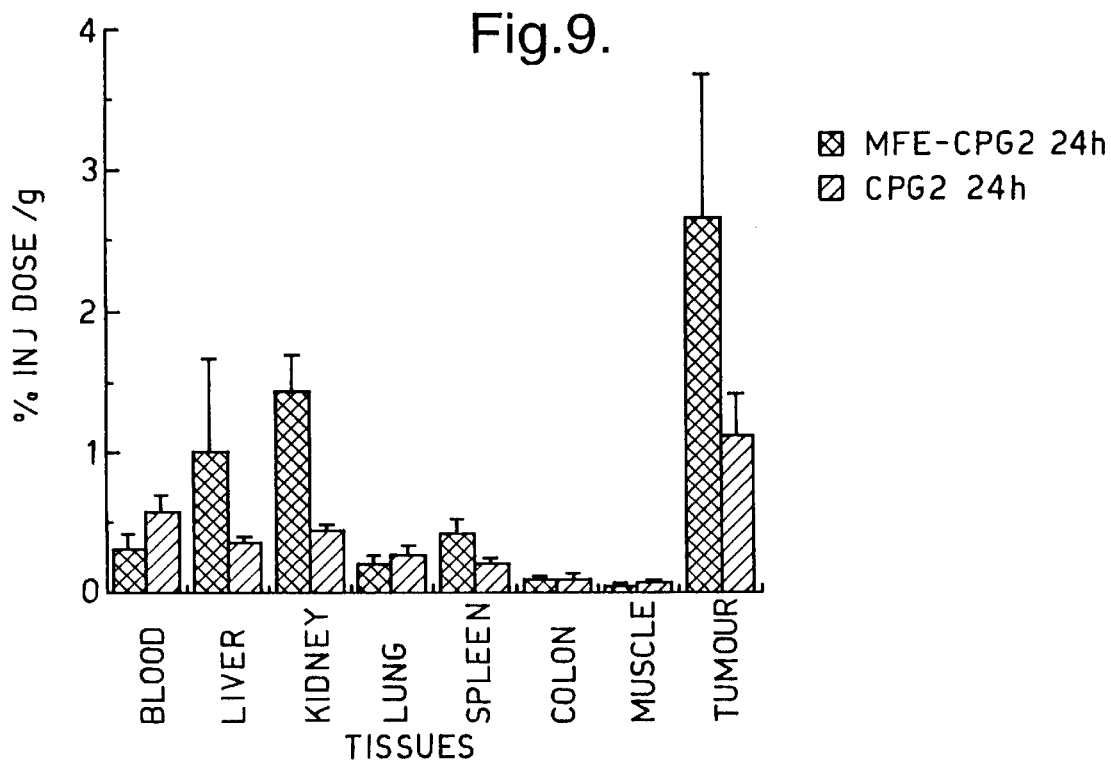
Figure 10:
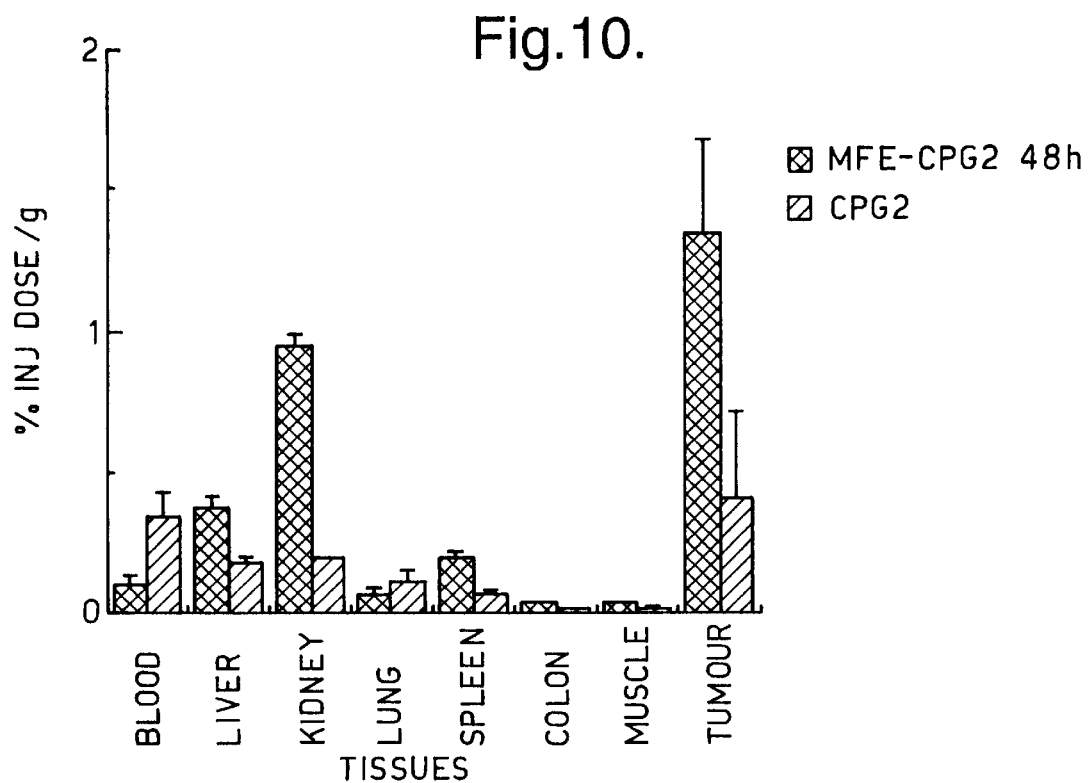

FIGS. 9 and 10 show the localisation in the LS174T colon xenograft of 125I MFE23-CPG2 and $^{125}$I CPG2. Results are expressed as percent injected activity per gram of tissue at 24 hours (FIG. 9) and 48 hours (FIG. 10).

Figure 11:
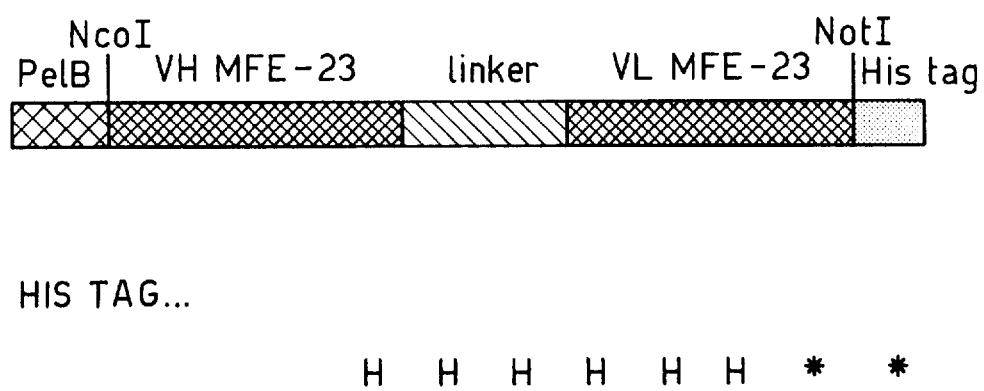

FIG. 11 is a schematic representation of MFE-23 subcloned for expression containing 6×His at the C-terminus. For antibody expression the vector contains a Pel B signal sequence which directs scFv into the bacterial periplasm; from here the scFv is released into the supernatant. * Denotes a stop codon. The nucleotide and amino acid sequences of FIG. 11 are SEQ ID Nos. 7 and 8 resectively.

EXAMPLE 1

Generation of an Antibody

Insertion of antibody genes into filamentous bacteriophage makes it possible to generate and screen libraries of 10$^7$ or more antibodies. Each phage expresses an antibody on its surface and contains the corresponding antibody gene. Genes which encode antibodies with desired characteristics are readily selected and their antibodies expressed as soluble proteins in *Escherichia coli*. This system has been used to produce an antibody to carcinoembryonic antigen with higher affinity and better tumour specificity than antibodies currently in use. The results suggest the phage system will be the method of choice for production of antibodies of general diagnostic and therapeutic use. The content of this Example has been reported in ref 15.

Radiolabelled antibody to carcinoembryonic antigen (CEA) can be used to image colorectal tumours and may be useful for therapy if targeting efficiency can be improved[1]. Antibodies of higher affinity may achieve this[2] and improved tumour specificity would also be of value. Phage technology is a new process for producing antibodies which is based on the display of functional antibody fragments on the surface of bacteriophage[3] (for review see ref 4). Large libraries of such antibodies can be made and cloned antigen binding phage obtained from these after a few rounds of (antigen driven) selection[5]. Phage technology also enables selection of antibodies with desired characteristics. For instance, high affinity antibodies and antibodies which dissociate slowly from their antigen may be isolated by manipulating the selection conditions[6]. The utility of the phage system is illustrated here by production of an antibody to CEA with improved characteristics for tumour targeting.

Figure 1:
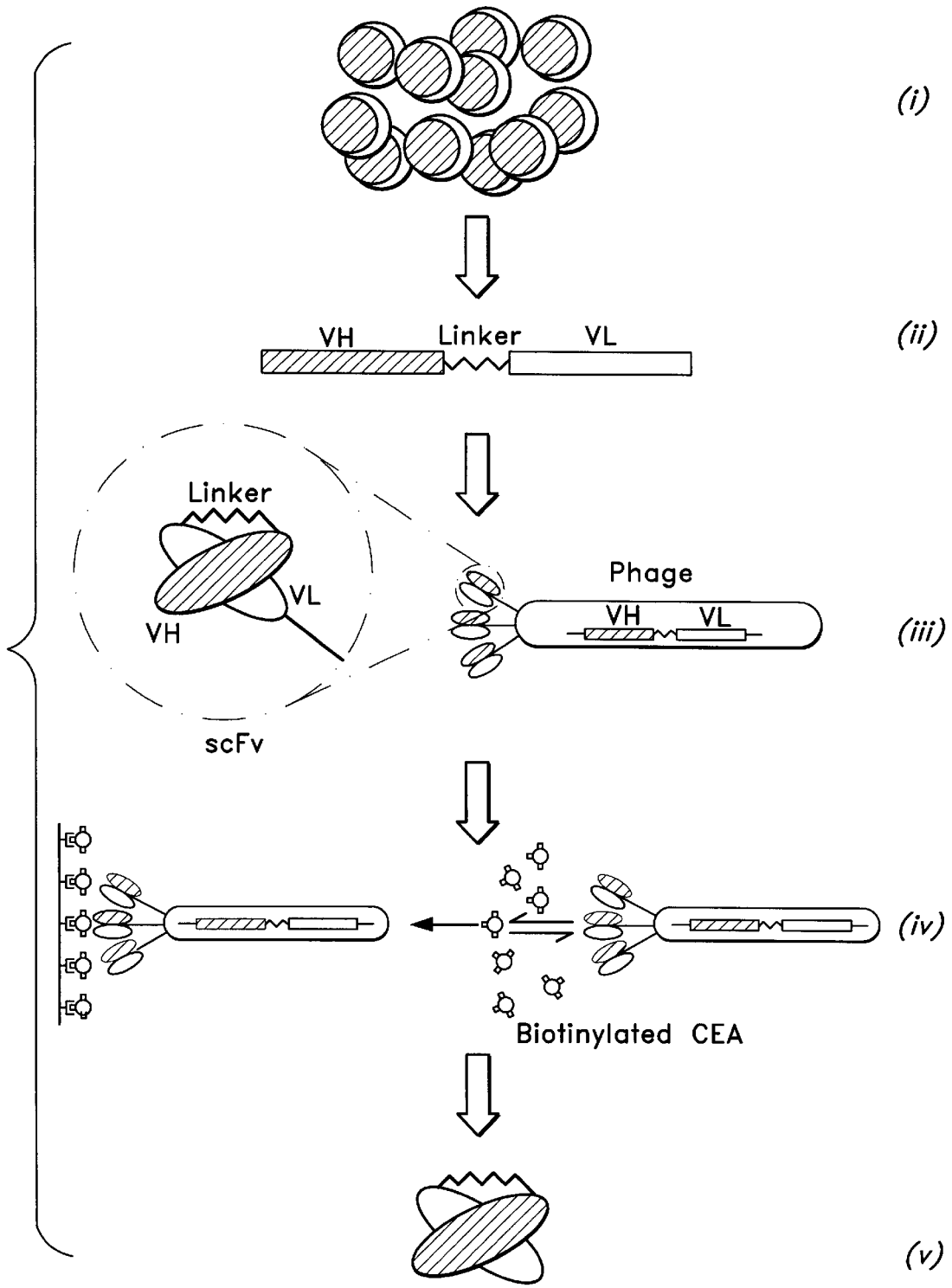
FIG. 1 shows a method of producing an scFv fragment in phage. In step (i), lymphocytes of an immunised mouse are used as a source of mRNA, and cDNA of antibody V-genes is prepared. In step (ii), antibody V-genes are amplified by PCR from the cDNA and subsequently assembled with linker into scFv. In step (iii), linked V genes are cloned into phage and the gene products are displayed on the surface of the phage as scFv fragments. In step (iv), phage which bind to CEA are selected by capture on streptavidin-coated magnetic beads. In step (v), soluble scFv is produced in bacteria for clinical use.

Mice were immunised with CEA (as for the production of conventional monoclonal antibodies) because mRNA from the spleen of immunised animals is greatly enriched for the desired antibody genes and provides a convenient starting point. The antibody variable region genes were amplified from cDNA with specific primers and cloned as a single chain Fv (scFv) (VH and VL joined by a flexible linker) into bacteriophage vectors producing a library of 10$^7$ members. The steps in this process are outlined in FIG. 1. Antibody with specificity for CEA was selected by allowing the phage library to bind biotinylated CEA and subsequently capturing bound phage with streptavidin coated beads[6]. The selected phage were amplified in number by infection and overnight growth in *Escherichia coli*. Several rounds of selection were performed and the progress monitored by phase ELISA[3]. A positive reaction with CEA was obtained after the first selection (O.D. 0.13 compared to 0.013 for the original library) and the strength of the signal increased with two successive rounds to O.D. 1.12. At this point individual clones were examined by DNA sequencing: of 25 clones sequenced at least 9 different ones were identified showing that there were different anti-CEA antibodies present. To obtain a scFv which bound CEA at low concentrations (i.e. high affinity) we performed a further two rounds of selection using a low concentration of biotinylated CEA (5 nM) and then re-analysed the library. Thirty four of 50 of the individual clones were positive in ELISA and DNA sequencing revealed that the 5 with the strongest ELISA signal were from the same clone. This clone was named MFE-23.

MFE-23 was subcloned for expression as a soluble scFv linked to a C-terminal myc tag to aid identification during protein purification. Protein production (approximately 20 mg per liter) from cultures of bacteria was obtained after 24 hours and the scFv was purified on CEA-Sepharose affinity chromatography and by size exclusion gel filtration. The dissociation constant (Kd) of MFE-23 was shown by fluorescence quench to be 2.5+/−1.3 nM, indicating the high affinity binding to CEA by comparison with a Kd of 25 nM in the same assay for A5B7, a monoclonal antibody which has produced some of the best colorectal tumour targeting to date[1]. Immunohistochemistry with the purified scFv using a second antibody directed against the myc tag showed in a typical CEA-reactive pattern in 10/10 human colorectal adenocarcinomas. The specificity against a range of normal human tissues was examined and the only reactivity was weak and with normal large bowel—this is in contrast to many anti-CEA monoclonal antibodies which commonly show cross reaction with a variety of normal tissues[7]. In particular, we found that the scFv bound to human colorectal adenocarcinoma but did not bind to the following normal tissues: liver, kidney, large intestine, tonsil, lung, brain, testis, ovary, cervix, breast, blood films, placenta, spleen, thyroid, oesophagus, stomach, pancreas, lymph node and skeletal muscle.

Figure 2:
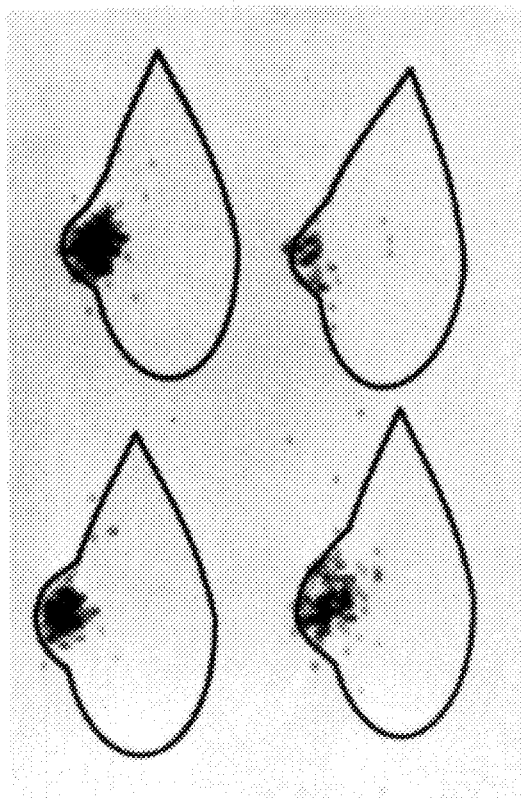
FIG. 2 shows the localisation of $^{125}$I-MFE23 in human colonic carcinoma xenografts. The images are gamma camera images at 29 hours (lower pair) and 35 hours (upper pair) after injection.

Tumour localisation in vivo was studied using LS174T human colorectal tumour xenografts in nude mice. FIG. 2 shows tumour imaging using [125]Iodine labelled MFE-23; only tumours are visible. In separate experiments tissues were removed and localised radioactivity assessed; results showed tumour: blood ratios of 11:1 at 24 hours after administration of MFE-23 and 53:1 at 48 hours.

MFE-23 is the first example of a high affinity, high specificity anti-tumour antibody produced by phage technology and our data indicate that it has potential for improved imaging and therapy of colorectal cancer. However, the system is not limited to this purpose as antibodies with desired characterises for a wide range of applications may be obtained in the same manner. Antibodies produced using phage technology also have the advantage that their genes are already cloned so genetically engineered antibody derived products such as fusion proteins of antibody with enzymes or toxins can be readily produced[4]. The ease of isolation and favourable combination of characteristics of MFE-23 illustrate the power of this approach and suggest that the phage antibody system will be used to produce the antibodies of the future.

EXAMPLE 2

A COMPARISON OF AN scFv ACCORDING TO THE INVENTION DERIVED FROM A FILAMENTOUS PHAGE LIBRARY WITH AN scFv DERIVED FROM A MONOCLONAL ANTIBODY scFvs can be either derived from a monoclonal antibody or produced directly using filamentous phage technology where antibodies with desired binding and purification characteristics can be readily selected from libraries. To test the hypothesis that the latter approach is more useful, we compared two anti-CEA scFvs produced by these two different approaches. Our study showed that, both in the purification process and in the biodistribution pattern, MFE-23 produced by filamentous phage technology gave favourable results compared to A5-SC which is derived from the monoclonal antibody A5B7. This indicates the value of the filamentous phage approach for obtaining tumour targeting scFvs.

Methods and materials:

Cloning of scFvs:

A5-SC: A chimeric recombinant Fab (rcFab) with Fv derived from A5B7 monoclonal anti-CEA and with human constant regions[16] was used as a source of plasmid DNA encoding the A5B7 variable regions. A5B7 VH was restricted using the enzymes Pst I and BstE II, isolated by electrophoresis in 2% NuSieve Agarose and purified using the Promega "Magic PCR" DNA purification system. A5B7 VL was obtained from the same rcFab plasmid using PCR with primers VKBACK[17] and forward primer VK4FOR-Not 1[18] to create a Not I site at the 3' end. The PCR fragment was purified using the Promega "Magic PCR", purification system and cut with Sac I and Not I. A5B7 VH and VL were sequentially cloned into their corresponding restriction sites in a scFv pUC 119 expression plasmid to give the construct A5-SC[19].

MFE-23: MFE-23 was produced by filamentous phage technology as described in Example 1, and subcloned into the same scFv pUC 119 expression vector as A5-SC.

Expression of scFvs in E. coli:

XL1 Blue (Stratagene) E. coli cells, transformed with the plasmids, were shaken at 37° C. in 2 X TY medium with 100 μg/ml ampicillin and 0.1% glucose until an O.D. of 0.9 at 600 nm. Protein expression was then induced by addition of 1 mM isopropyl beta-D thiogalactoside and overnight incubation at 30° C. Cells were then pelleted and the supernatant containing the scFv decanted and stored at 4° C. Anti-CEA activity was tested for both scFvs by ELISA, using CEA coated wells (2 μg/ml). Bound scFv was detected by 9E10 anti-myc antibody (a gift from Dr. Gerrard Evan, ICRF London) followed by anti-mouse Ig-HRP conjugate (Jackson) and visualised using the substrate o-phenylenediamine dihydrochloride (Sigma).

Purification of scFvs b affinity and size exclusion gel chromatography:

Supernatant was concentrated 5–10 times using a Spiral cartridge (S1Y10 Amicon) and dialysed against PBS/Az (50 mM phosphate, 150mM NaCl pH 7, containing 0.02% sodium azide). The concentrate was applied to a 7 ml CEA/Sepharose-4B column, containing 7 mg of CEA. Unbound material was removed with PBS/Az. Bound A5-SC was eluted in 2 stages. First, 50 mM diethylamine (pH 11) was applied and second, 3M ammoniumthiocyanate. Bound MFE-23 was eluted with 50 mM diethylamine (pH 11). In both cases the diethylamine fractions were immediately neutralised with 1M phosphate buffer (pH 7.5). The collected fractions were pooled, dialysed against PBS/Az, concentrated and applied to Sephacryl S-100 (S-100) (Pharmacia) for separation by size exclusion. Isolated, purified scFvs were further concentrated to 0.5–1 mg/ml and stored at 4° C. Anti-CEA activity of both antibodies was confirmed with a positive ELISA.

pI of scFvs:

The isoelectric focusing points of the scFvs were obtained using an Amphaline PAG plate pH 3.5–9.5 (Pharmacia) in accordance with manufacturers instructions.

Iodination:

75 μg of A5-SC and MFE-23 were iodinated with 0.5 mCi of 125-I using the Chloramine T/L-Tyrosine method[20]. Radiolabelled products were tested by thin layer chromatography to demonstrate efficiency of 125-I uptake, and by application to a 1 ml CEA/Sepharose column, containing 1 mg of CEA, to test CEA binding prior to administration to the mice. The stability of the radiolabelled products was tested by gel filtration on S-100.

Xenograft studies:

Radiolabelled antibody was administered via the tail vein of nude mice bearing the LS174T human colorectal carcinoma xenograft[21]. Each mouse received 4.3 μg/30.12 μCi of A5-SC or 4.3 μg/7.73 μCi of MFE-23. Mice were sacrificed at 24 h and 48 h, and tissues were removed and assessed for activity using a gamma counter. 4 mice were used for each time point.

Results:

Yields during purification:

Yields of the scFvs were estimated after affinity chromatography and size exclusion gel filtration, using optical density measured at 280 nm. The extinction coefficient for A5-SC was calculated to be 0.6 and for MFE-23 0.7, using the formula: molecular weight/number of tyrosine residues× 1000+ number of tryptophan residues×5000. All results are expressed as protein yield from 1 liter of supernatant. After affinity chromatography and concentrating the protein, 0.65 mg A5-SC was obtained, compared to 4.3 mg for the MFE-23. After S-100 gel filtration and concentration the protein yield of A5-SC appeared to be very low, only 0.2 mg in comparison to 2.76 mg for the MFE-23 final product, which was 13.8 times higher. The elution profile from the S-100 showed two peaks with A5-SC, compared to only one peak for the MFE-23. The MFE-23 peak and the second A5-SC peak corresponded to a molecular weight of 27 kD, which is expected for a monomer scFv. The first peak of the A5-SC S-100 profile was considered to be dimer A5B7 and this was tested and confirmed by SDS-PAGE.

pI of scFvs:

The isoelectric focusing points showed that A5-SC is more basic than MFE-23, as the pI of A5-SC was 9–9.5, compared to a lower pI of 4.5–5.5 for MFE-23.

Stability after iodination:

The stability of the scFvs after radiolabelling was tested by gel filtration on S-100. The elution profile of A5-SC showed a single peak. There was no sign of dimer formation and no aggregation was detected. The S-100 profile of MFE-23 similarly showed one peak. These results confirmed the physical stability of A5-SC monomer and MFE-23 after iodination.

The CEA-activity of both radiolabelled products was tested by binding to CEA/Sepharose. The percent of counts recovered was calculated to be 30.8% for the A5-SC and 38.7% for the MFE-23.

Tumour localisation of A5-SC and MFE-23 in human tumour xenografts.

The biodistribution of A5-SC and MFE-23 was examined at 24 and 48 hours after administration. Percent injected activity per gram of tissue and tissue to blood ratios were assessed. 1.2% of the injected activity of A5-SC was localised in the tumour at 24 hours after administration compared to 3.2% of MFE-23 (FIG. 4). At 48 hours these absolute amounts in the tumour dropped for both proteins, giving values of 0.46% for A5-SC and 1.2% for MFE-23 (FIG. 4). However, due to the rapid blood clearance of the scFvs these amounts resulted in favourable tumour to blood ratios at this time point. These were 11:1 for A5-SC and 24:1 for MFE-23 (FIG. 5). The 24 h time point gave ratios of 6:1 for A5-SC and 13:1 for MFE-23.

For A5-SC a significant amount of activity was detected in the kidney. The % injected dose at both time points was even higher than that detected in the tumour; 3.2% at 24 hours and 2.4% at 48 hours (FIG. 4). This gave rise to high kidney to blood ratios (19.7:1 at 24 h and 97.2:1 at 48 h). MFE-23 also showed some activity in the kidney, but this was much lower than that observed with A5-SC giving kidney to blood ratios of respectively 4.7:1 at 24 h and 9.6:1 at 48 h. In both instances this was less than the amount localised in the tumour.

Uptake of A5-SC was also observed in liver and spleen, giving tissue to blood ratios of 15.6:1 and 8.6:1 respectively at 48 hours. This is in contrast with MFE-23, which did not show localisation in these organs. The liver s and kidney uptake of A5-SC did not appear to be due to aggregation as no high molecular weight material was detected in the S-100 profile of A5-SC after radiolabelling.

Conclusion:

This Example describes a comparative study between two anti-CEA scFvs derived by different approaches, A5-SC being derived from a monoclonal antibody while MFE-23 is produced by phage technology. The results showed a favourable biodistribution, with higher absolute amounts and better tumour to blood ratios for MFE-23 compared to A5-SC. MFE-23 was also easier to purify.

EXAMPLE 3

$^{99m}$TC RADIOLABELLING OF AN ANTIBODY ACCORDING TO THE INVENTION WITH A C-TERMINAL CYSTEINE FOR COLORECTAL TUMOUR IMAGING scFvs have potential for clinical imaging studies because of their rapid tumour penetration and the high tumour to tissue ratios at early time points. Free thiol groups are necessary for labelling scFvs with technetium. To achieve this a vector which enabled a free cysteine to be linked to the C-terminus of scFvs was constructed. MFE-23 was cloned into this vector and cysteine-tagged MFE-23 was labelled with technetium using a D-glucarate transfer method. The radiolabelled product appeared to be stable both in vivo and in vitro and showed favourable tumour to blood ratios in vivo at early time points; 4:1 at 24 h and 8:1 at 48 h.

In comparison with iodinated MFE, $^{99m}$Tc labelled MFE showed a higher % injected activity in the tumour.

Materials and methods:

Expression vector and cloning of MFE-cys:

To create a new expression vector with a cysteine in the C-terminal tail, inverse PCR site directed mutagenesis[28] was used to replace a histidine in the previously described[19] pUC119 based expression vector containing a C-terminal hexahistidine tag. Modification was achieved using 25 cycles of PCR with the oligonucleotides Cys-His-For (5'-TGGTGATGACATGCGGCCGCCCGTTTGAT-3', SEQ ID No: 3) and His6-Bak (5'-TCATCACTAATAAGAATTCACTGGCCG-3', SEQ ID No: 4) followed by self ligation. Clones containing the required sequence (FIG. 6) were identified by DNA sequencing. MFE-23 was subcloned into this vector as an Nco1/Not1 fragment.

Expression of MFE-cys in E. coli:

E. coli 'Sure' cells (Stratagene) were transformed with the plasmid construct shown in FIG. 6. Cells were shaken at 37° C. in a 2 X TY medium with 100 μg/ml ampicillin and 0.1% glucose until an optical density of 1.0 at 600 nm was obtained. Protein expression was induced by adding 1 mM isopropyl beta-D thiogalactoside overnight at 30° C. The cells were then pelleted and the supernatant containing MFE-cys decanted and stored at 4° C.

Purification of MFE-cys:

Supernatant was concentrated 10 times using a Spiral cartridge (S1Y10 Amicon) and dialysed against PBS/Az (50 mM phosphate, 150 mM NaCl pH 7, containing 0.02% sodium azide). The concentrate was applied to a CEA/Sepharose-4B column, containing 7 mg of CEA. Unbound material was washed through with PBS/Az. Bound MFE-cys was eluted with 50 mM diethylamine (pH 11), after which the fractions containing the protein were immediately neutralised with 1M phosphate buffer (pH 7.5). The collected fractions were pooled, dialysed against PBS/Az and stored at 40° C. Pooled eluates were then concentrated using Diaflo ultrafiltration membranes (YM10 Amicon), after which the concentrated material was purified by size exclusion gel filtration on Sephacryl S-100 (Pharmacia). The yield of MFE-cys during the purification process was estimated using the optical density measured at 280 nm. The extinction coefficient for MFE-cys was calculated to be 0.7 using the formula: molecular weight/number of tyrosine residues×1000+number of tryptophan residues×5000. Purified MFE-cys monomer was concentrated and stored at 4° C.

Labelling of MFE-cys:

MFE-cys was radiolabelled with $^{99m}$Tc using a $^{99m}$Tc-D-glucarate transfer method[22]. 1 ml of $^{99m}$Tc sodium pertechnetate (40.5 mCi) was added to 12.5 mg of monopotassium D-glucarate, 16.8 mg of sodium bicarbonate and 100 μg of stannous chloride (stannous chloride was made up directly before use at a concentration of 0.2 mg/ml). This solution was left for 1 min at room temperature. Then 0.5 ml was mixed with 200 μg MFE-cys in PBS/1 mM EDTA. The mixture was incubated at room temperature for 30 min and then applied to a PD 10 column (Pharmacia; primed with 3% human serum albumin in PBS) to separate the radiolabelled protein from the free pertechnetate. The efficiency of $^{99m}$Tc uptake was tested by thin layer chromatography, using acetonitrile/water (30:20) as running solvent. An aliquot (100 μl) of diluted radiolabelled scFv (1:30 in PBS/Tween 20) was applied to a 1 ml CEA-sepharose column, containing 1 mg of CEA, to test CEA-binding. The column was washed with 8 volumes of PBS/0.05% Tween 20 and bound material was obtained by adding 3M ammoniumthiocyanate. Further, the stability of the labelled scFv was tested by applying the product (diluted 1:30) to Sephacryl S-100. To test the stability of the radiolabelled product in vivo serum taken from mice injected with the labelled scFv 24 h after administration was also applied to Sephacryl S-100. Stability of the $^{99m}$Tc-labelled product was also tested by gel autoradiography as follows: radiolabelled MFE-cys was subjected to SDS-PAGE using a 15% non-reducing acrylamide gel. The protein was then Western blotted onto Immobilon P (Millipore), and visualised by autoradiography using Kodak X-Omatic cassette and Hyperfilm-MP film (Amersham).

Xenograft study:

The human colon adenocarcinoma cell line LS174T was used to develop a xenograft tumour model[11]. $^{99m}$Tc radiolabelled MFE-cys (11 μg/36.4 uCi per mouse) was administered via the tail vein. Mice were killed at 24 h and 48 h following administration and blood, liver, kidney, lung, spleen, colon, muscle, femur (only for technetium labelled MFE-cys) and tumour were removed. Activity was assessed by counting on the gamma counter (LKB, Bromma, Sweden, Wallac 1284 Compugamma) after digestion with 7M KOH. Activity was expressed as % injected dose per gram of tissue. 4 mice were used for each time point.

Results:

Yields during purification of MFE-cys:

After affinity chromatography and concentrating a protein yield of 13.3 mg of MFE-cys was obtained from 4 liters of supernatant. The elution profile from the Sephacryl S-100 showed two peaks; the second peak corresponded with a molecular weight of 27 kD, the correct molecular weight for monomer MFE-cys. The first peak was shown to be dimer MFE-cys on a non-reducing SDS-PAGE. After concentrating MFE-cys monomer a final yield of 8 mg was achieved, compared to only 1 mg from the dimer peak (ratio 8:1). Purity of monomer MFE-cys was confirmed on SDS-PAGE, showing only one band at the correct molecular weight.

Analysis of $^{99m}$Tc-labelled MFE-cys:

MFE-cys was radiolabelled using a $^{99m}$Tc-D-glucarate transfer method. Thin layer chromatography showed a $^{99m}$Tc incorporation within the protein of more than 80%. CEA-binding activity of the radiolabelled product appeared to be very good; after applying the radiolabelled product to the CEA/Sepharose column 55% of counts was recovered in the bound fraction.

Its stability in vitro was confirmed by applying the radiolabelled product to Sephacryl S-100; little degradation was detected. No sign of dimer formation was seen and no aggregation was detected. In accordance with this result, gel autoradiography showed only one band at the correct molecular weight for this scFv. When serum from mice injected with $^{99m}$Tc-labelled scFv taken 24 h after administration was applied to Sephacryl S-100, only one peak at the correct molecular weight was observed, which also confirmed its stability in vivo.

In vivo studies:

The biodistribution of $^{99m}$Tc-labelled MFE-cys was examined over a period of 48 hours. Percent injected activity per gram of tissue and the tissue to blood ratios were assessed. The results are shown in FIG. 7 and FIG. 8. These results demonstrate that, at both time points, $^{99m}$Tc-labelled MFE-cys showed approximately 4% of injected activity was localised in the tumour at 24 h and at 48 h 2.4% was localised. These amounts resulted in favourable tumour to blood ratios at both time points, because of the fast clearance of this scFv. These were 4:1 at 24 h and 8:1 at 48 h.

Significant activity in normal tissues was only observed in the kidney. Technetium labelled MFE-cys showed a higher percent of injected activity in the kidney than in the tumour which resulted in high kidney to blood ratios at both time points; respectively 10:1 at 24 h and 17:1 at 48 h.

Conclusion

Technetium labelled MFE-cys showed favourable biodistribution characteristics in vivo for early diagnostic imaging. Technetium's ready availability, its low costs, the ideal properties for gamma camera imaging, the low patient radiation exposure per millicurie of radionuclide and finally the fact that thyroid blocking agents are not necessary, make technetium much more practical for immunoscintigraphy.

EXAMPLE 4

THE BIODISTRIBUTION OF AN ANTIBODY ACCORDING TO THE INVENTION FUSED TO CARBOXYPEPTIDASE G2 (CPG2)

This example compares the biodistribution of $^{125}$I MFE23-CPG2 and $^{125}$I CPG2 in the LS174T tumour model.

Small pieces of xenograft tissue were placed subcutaneously in the flanks of nude mice. The tumours were grown for 2–3 weeks before commencing the experiment. There were 4 mice/group/time point.

1. The first group (12 mice) received 2.8 μg/3 μCi/8.6 U/0.2 ml $^{125}$I MFE23-CPG2 intravenously into the tail vein.
2. The second group (8 mice) received 2.8 μg/21 μCi/0.2 ml 125I CPG2 intravenously into the tail vein.

The mice were bled and tissues removed at 24 and 48 hours.

The percent injected activity per gram of tissue was assessed at the two time points. The results are shown in FIG. 9 and FIG. 10. After 24 hours, $^{125}$I MFE23-CPG2 showed a tumour: blood ratio of 9.4:1, whereas $^{125}$I CPG2 should a ratio of 2:1. After 48 hours, $^{125}$I MFE23-CPG2 showed a ratio of 12.6:1 whereas 125T CPG2 showed a ratio of 1.1:1. Thus, $^{125}$I MFE23-CPG2 shows favourable localisation to tumour.

EXAMPLE 5

PURIFICATION OF AN ANTIBODY ACCORDING TO THE INVENTION USING A His TAG

This Example concerns a new Procedure for the purification of an antibody according to the invention. Insertion of a hexa-histidine tail fused at the C-terminus of the antibody provides an affinity tag which selectively binds to transition metal ions immobilised on an Iminodiacetic acid (IDA) derivitised solid phase matrix. This method proved to be superior to standard CEA antigen affinity chromatography in the following ways: (1) A higher yield was produced (10 mg per liter as opposed to 2.2 mg per liter of bacterial supernatant). The latter figure was largely affected by the limited availability (size of the column) of immobilised CEA antigen. (2) Scale-up was relatively simple and less costly. (3) The risk of tumour derived antigen leaching from the column is eliminated. Results showed that immobilised $Cu^2$ ions are more effective that $Ni^{2+}$ and $Zn^{2+}$ ions in retaining the His tagged product giving a 90% pure product on elution. Clinical grade material was generated using size exclusion chromatography to remove aggregated material, and Detoxi gel to remove bacterial endotoxins. Validation assays to measure DNA, copper and endotoxins were performed to assess the levels of contaminants. MFE-23 His retained 84% antigen binding after 6 months storage at 4° C. and >75% after radiolabelling. Further experiments confirmed that the His tail did not affect biodistribution and tumour localisation in nude mice bearing human colorectal tumour xenografts.

Materials and methods.

The preparation of clinical grade material requires particular precautions which are not necessary in the preparation of laboratory products. The clinical grade scFv produced here was in accordance with the guidelines specified in the Cancer Research Campaign control operation manual for recombinant products[32]. A summary of the guidelines for the quality and safety of clinical products include:

1. Designated sterile work areas and equipment which will prevent contamination of the purified product.
2. Full details of product development including expression systems and DNA sequencing.
3. Preparation of a clinical seed lot including testing for homogeneity and reactivity on storage.
4. Purification details and reproducibility.
5. Final product characterisation including contamination levels, potency, biological activity and toxicity.

Standard operating procedures (SOP's) have been drawn up for each individual stage of the production process outlined above.

Subcloning and expression of the polyhistidine tail

The gene encoding MFE-23 was subcloned into a pUC 119 expression vector to contain 6×His at the C-terminus (Figure 11-MFE-23 His vector). The construct was transfected into E. coli TG1 cells using electroporation and plated onto 2×TY agar containing 100 μg/ml ampicillin and 1% glucose. An individual colony was used to produce a seed lot in accordance with safety guidelines and DNA sequencing was employed to confirm identity. For expression, seed lot aliquots were cultured in 2×TY medium containing 100 μg/ml ampicillin and 1% glucose at 37° C. shaking for 16–20 h. Cells were grown until a cell density of 0.9 at an optical density (OD) 600 nm was achieved. Production of scFv was promoted by the addition of 1 mM isopropyl β-D-thiogalactoside and the temperature reduced to 30° C. for a further 16 h. Cells were pelleted at 11,300×g and the supernatant containing the MFE-23 His was passed through 0.45 μm followed by 0.2 μm 1 liter Nalgene disposable filters (Fisons, Lougiborough, UK).

Concentration and dialysis of MFE-23 His supernatant

The bacterial supernatant was concentrated using an Amicon CH2 ultrafiltration system (Amicon, Stonehouse, Glocestershire, UK) incorporating a RA2000 reservoir and S1Y10 spiral cartridge with a molecular weight cut off of 10 kDa. To sterilise the ultrafiltration system for the clinical grade material it was washed in Hospec neutral detergent followed by 0.1M sodium hydroxide and pyrogen free water (Baxter, Norfolk, UK) to neutralise. MFE-23 His culture supernatant (1–4 liters) was concentrated to 200–300 ml and pressure dialysed against sterile phosphate buffered saline pH 7.2 (Dulbecco's PBS-Sigma, Poole, UK). The crude MFE-23 His was centrifuged at 6,300×g for 20 min at 4° C. and re-filtered using 0.45 μm and 0.2 μm Nalgene filters to sterilise and remove any large protein aggregates which may have formed during the concentration steps.

Purification

IMAC purification was optimised on a small scale using non sterile conditions. Clinical purification procedures were performed under rigorous conditions, using sterile glassware, disposables and chemicals. All buffers were made with pyrogen free water. Imidazole solutions were buffered with Dulbecco's sterile PBS containing 1M sodium chloride (NaCl) to suppress ionic interactions, thereby improving selectivity of the metal for the histidine ligands[33].

IMAC

A 10/2.5 cm Econocolumn (Bic-Rad, Hemel Hempsted, UK) was packed with 40 ml chelating Sepharose fast flow (Pharmacia Biotech, St Albans, UK) and equilibrated under gravity with 100 ml water. Metal ions (100 ml) were loaded as 0.1M copper sulphate, zinc chloride or nickel chloride (Sigma) in water and washed through with the same volume of equilibrium buffer (PBS/1M NaCl). NaCl was added to the concentrated dialysed supernatant to a final concentration of 1M to prevent leaching of metal ions from the column[33]. Up to 300 ml supernatant was loaded and the unbound material collected. Competitive elution was carried out using an imidazole gradient of 40, 60, 80, 100 and 120 mM, collecting 250 ml batchwise of bound product at each step. The column was regenerated by stripping metal ions with 100 ml of 50 mM EDTA and re-equilibrated with several column volumes of water.

All fractions were dialysed into PBS to remove salt, eluting agents and any metal ions which may have leached from the column. The fractions were then pooled and concentrated using stirred cell ultrafiltration and a PM10 membrane (Amicon) for SDS PAGE analysis. To increase recovery of clinical material all dialysed fraction excluding the 120 mM imidazole fraction were subsequently pooled and reapplied to the column.

Gel filtration

The IMAC purified material was further purified by size exclusion to remove aggregates and metal ions. The concentrated, dialysed 0.22 µm sterile filtered (Gelman, Northampton, UK) 120 mM imidazole fraction was applied to a 350 ml Sephacryl S-100 (Pharmacia Biotech) column (XK 16/100-Pharmacia Biotech). Fractions were measured at OD 280 nm, relevant fractions were pooled and concentrated, using stirred cell ultrafiltration and stored at 4° C.

Affinity chromatography 2 liters of MFE-23 His which had been concentrated and dialysed in PBS (400 ml) was purified using a 6 ml cyanogen bromide activated Sepharose 4B (Pharmacia Biotech.) affinity column coupled to CEA (8 mg). CEA was obtained from a patient's colorectal tumour liver metastasis by extraction using perchloric acid[34]. One column pass of 30 ml supernatant per run was performed.

Bacterial Endotoxin removal

A 10×2.5 cm Econocolumn (Bio-Rad) was packed under gravity with 10 ml of Detoxi gel (Pierce Warriner. Chester, UK) and equilibriated with sterile PBS. 10 ml of the concentrated purified product was loaded, carefully mixed with the gel and incubated overnight at room temperature in a sealed column. The product was eluted by washing with 30 ml PBS.

Final product testing

Samples at each purification stage were analysed for endotoxin levels using Limulus ameobocyte lysate (LAL) gel clot vials (Atlas bioscan. Bognor Regis, UK) according to the manufacturers' recommended instructions; a further aliquot (three times the patient dose) was tested by injection into rabbits (Safepharm Laboratories; Derby, UK) Bacterial supernatant containing MFE-23 His, semipurified MFE-23 His and the final product were tested for the presence of bacterial DNA using the Digoxigenin (DIG) DNA labelling and detection assay (Boeringer Mannheim, Lewes, UK). A probe was constructed using a mixture of equal proportions of MFE-23 plasmid DNA and total bacterial DNA. DIG labelled DNA probes were detected after hybridisation. to target samples by enzyme-linked immunoassay using an anti-DIG alkaline phosphatase conjugate. The probe was sensitive to 12 pg of DNA. The final product was also assayed for $Cu^{2+}$ content and compared with earlier purification stages, using flame photometry (Trace Element laboratory-University of Surrey). An aliquot was also protein sequenced using amino acid analysis by the CRC protein sequencing facility (University college of London) to confirm homogeneity of the final product and cleavage of the pelB leader sequence in the periplasm. Stability of the antibody was assessed by storing aliquots at 4° C. and −70° C. and subsequently analysing samples at certain time intervals using a Superose 12 HR 10/30 (Pharmacia) FPLC column. Retention of antigen binding following 6 months storage at 4° C. was measured by applying a known amount of purified antibody to the CEA affinity column (refer to section 2.7) and quantitating the % bound (specific activity). These values were compared by applying a known amount of MFE-23 His previously purified using the same column.

Iodination of MFE-23 His

Radiolabelling of MFE-23 His with $^{125}$Iodine (125I) was performed using the Chloramine T method[35]s. Typically 67–250 µg of purified product in 0.5 ml was radiolabelled to give specific activities of 167–481 MBq/µg.

Analysis of radiolabelled product

Thin layer chromatography (TLC) was performed to measure % $^{125}$I incorporation. Antigen binding was also assessed by applying a dilution of the radiolabel to a CEA coupled Sepharose 4B (1 mg CEA; 1 ml column volume). The unbound fraction was washed through with 2 column volumes of PBS and the bound fraction with the same volume of 3M ammonium thiocyanate. A control scFv B1.8 which is not specific for CEA and MFE-23 containing a c-myc tag (MFE-23 myc) were tested as a comparison. The unbound and bound fractions were analysed for $^{125}$I activity using a gamma counter. Stability assessments were carried out by applying a sample of the radiolabel and unlabelled product to a 15% SDS PAGE minigel. The $^{125}$I-MFE-23 His was visualised by autoradiography and the unlabelled product by Coomassie blue staining. $^{125}$I-MFE-23 His was also applied to a 100 ml Sephacryl S-100 column (115×1 cm). 1.5 ml fractions were collected and counted for $^{125}$I activity.

In vivo xenograft experiment

Tumour localisation and biodistribution of $^{125}$I-MFE His was carried out in nude mice bearing LS174T human tumour xenografts. MFE-23 myc which had been previously characterised, affinity assessed and shown to localise in human tumour xenografts (Example 1) was included as a comparison. Radiolabelled antibody was administered into the tail vein of mice, when the tumours were approximately 0.5 g in weight. Each mouse received 5 µg/10 µCi of $^{125}$I labelled antibody and 4 mice from each group were sacrificed 24 h later. Tissues and blood samples were removed, weighed, digested in 7M potassium hydroxide for 24 h and assessed for activity using a gamma counter.

Results

Optimising IMAC $Ni^{2+}$, $Zn^{2+}$ and $Cu^{2+}$ were compared for efficacy as metal ions for IMAC solid support. SDS PAGE electrophoresis showed that in general the majority of non specific proteins were washed through the column in the unbound fraction. Further impurities were eluted by competing with low concentrations of imidazole 10–40 mM. Increasing the concentration of imidazole to compete for metal binding sites results in elution of His tagged product. This stepwise imidazole gradient was useful for comparing the efficiency of antibody binding to $Ni^{2+}$, $Zn^{2+}$ and $Cu^{2+}$ immobilised metal ions and the level at which pure product eluted from the column. Any remaining product eluted when the column was stripped with EDTA. Impurities were present in all imidazole elution and EDTA fractions when the column was primed with $Ni^{2+}$. There was also visible leaching of $Ni^{2+}$ on imidazole elution reflecting the weak binding affinity of $Ni^{2+}$ to the column. In contrast, when the column was primed with $Zn^{2+}$ the imidazole gradient was more effective in producing pure product than when $Ni^{2+}$ was used. However, the 80–120 mM imidazole and EDTA fractions contained some remaining impurities. The best elution profile was produced by priming the column with $Cu^{2+}$ ions; pure product eluted at 60–120 mM imidazole and EDTA fractions. Although pure product also eluted in the EDTA fraction this could 20 not be further processed for clinical use due to the presence of high levels of copper ions which were difficult to remove even after extensive dialysis. This fraction was dialysed and reapplied to the column. Considering the results, copper was selected as the immobilised metal ion for clinical production of MFE-23 His. To ease handling large volumes of the clinical batch a step gradient of 40 and 120 mM imidazole concentrations was employed.

Impurities were separated by eluting with 250 ml 40 mM imidazole from pure product at 120 mM imidazole (250 ml) in a single chromatographic step.

Purity and yield

Gel filtration of the clinical grade MFE-23 His revealed that 90% of the product was in monomer form after one purification step. Large molecular weight material was effectively separated from the product The final product yield of the clinical batch was approximately 10 mg per liter of supernatant at OD 280 nm using the extinction coefficient of 0.7. The affinity purified material produced a 2.2 mg per liter yield with a single pass through the column.

Final product evaluation

The contamination levels of clinical grade MFE-23 His with bacterial endotoxins and copper at each chromatographic step are show in Table I.

TABLE I

Bacterial endotoxin and copper removal in each chromatographic step.

| Purification step. | Endotoxin Eu/ml | $Cu^{2+}$ $\mu M/l$ |
|---|---|---|
| Supernatant | 50,000 | — |
| $Cu^{2+}$ chelate column eluate pre dialysis (120 mM fraction | — | 75 |
| post dialysis (120 mM fraction) | 750 | 8 |
| Gel filtration S-100 eluate | 25 | 3.4 |
| Detoxi gel eluate (final product) | <2.5 | — |

The results showed that Detoxi gel was effective in removing at least one log scale of bacterial endotoxins from the purified scFv with no decrease in yield. The final product was also confirmed as non pyrogenic by in vivo rabbit testing. The extent of ligand leaching was also monitored by $Cu^{2+}$ analysis. Copper levels were largely reduced after extensively dialysing and very low levels are present in final product. DNA was not detected (sensitivity of assay=12 pg) in the final purified product. Protein sequencing of the first 15 N-terminal amino acids of the protein showed consistency with the DNA sequence. This also confirms that the pel B leader has been cleaved in the periplasm. Stability assessments at 4° C. and −70° C. up to 6 months showed one peak on FPLC analysis consistent with the molecular weight of scFv and no evidence of aggregation.

Retention of antigen binding on 6 months storage at 4° C. is shown in Table II. This indicated that an average value of 75% binding was achieved.

TABLE II

Specific activity of MFE-23 His purified using IMAC (a–c) and CEA antigen affinity chromatography (d). The specific activities were based on antibody levels recovered, as some losses occurred on dialysis and concentration steps. The mean % bound specific activity for the IMAC purified material (a–c) is 75%.

| Antibody applied to column (mg) | Unbound (mg) | Bound. (mg) | Specific activity. (%) |
|---|---|---|---|
| a. 2 | 0.35 | 0.76 | 69 |
| b. 1 | 0.23 | 0.68 | 75 |
| c. 0.5 | 0.09 | 0.40 | 81 |
| d. 1 | 0.10 | 0.83 | 89 |

Radiolabelled MFE-23 His

When the radiolabelled product was tested for % incorporation using TLC analysis the results demonstrated that 95–99% of the $^{125}$Iodine was bound to the antibody. Retention of antigen binding was assessed after radiolabelling by measuring the binding to antigen. A sample of radiolabelled clinical MFE-23 His batch was applied to the CEA column. Of the total number of counts recovered (1710 cpm), 435 cpm (25%) washed through in the unbound fraction and 1275 cpm (75%) eluted in the bound fraction. The unbound fraction was subsequently reapplied to the column and a further 58% of total counts loaded was recovered in the bound fraction. Samples of diluted radiolabelled MFE-23 myc and B1.8 were also applied to the CEA column. For MFE-23 myc 56% (23023 cpm) of total counts recovered (40901 cpm) bound to the column and 17878 cpm (43%) washed through the unbound. For the non specific control antibody B1.8 only 10% (1301 cpm) of the total recovered counts (12717 cpm) bound to the column and 89% (11416 cpm) was contained in the unbound fraction. The stability of radiolabelled product was determined by SDS PAGE and gel filtration, revealing it was monomeric, intact and unaggregated.

In vivo studies $^{125}$I-MFE-23 His localised in tumour selectively giving a therapeutic tumour to blood ration of 22:1. MFE-23 myc produced similar results with a tumour to blood ratio of 9:1. The uptake of MFE-23 His in normal tissues was also comparable to the previously characterised MFE-23 myc, except for high levels in the kidney, which is the main clearance pathway of the antibody.

REFERENCES

1. Begent RHJ: Targeted therapies: cell surface targets. In: Ponder B. ed. Cancer Biology and Medicine, vol. 2. Klewer Academic Publications, 1990; 161–184.
2. Schlom J, Eggensperger D, Colcher D, Molinolo A, Houchens D, Miller L S, Hinkle G & Siler K. Therapeutic advantage of high-affinity anticarcinoma radioimmunoconjugates. Cancer Res 1992; 52; 1067–1072.
3. McCafferty J, Griffiths A D, Winter G & Chiswell D J: Phage antibodies: filamentous phage displaying antibody variable domains. Nature 1990; 348; 522–554.
4. Hawkins R E, Llewelyn M B & Russell S J: Monoclonal Antibodies in Medicine. Adapting antibodies for clinical use. BMJ 1992; 305; 1348–1352.
5. Clackson T, Hoogenboom J J R, Griffiths A D & Winter G: Making antibody fragments using phage display libraries. Nature 1991, 352; 624–628.
6. Hawkins R E, Russell S J & Winter G. Selection of phage antibodies by binding affinity: mimicking affinity maturation. J. Mol Biol. 1992; 226; 889–896.
7. Nap M, Hammarstrom M-L, Borer O, Hammarstrom S, Wagner C, Handt S, et al. Specificity and affinity of monoclonal antibodies against carcinoembryonic antigen. Cancer Res 1992; 52; 2329–2339.
8. Goldenberg D M. Cancer imaging with CEA antibodies: historical and current perspectives. The International Journal of Biological Markers 1992; 7; 183–188.
9. Ledermann J A, Recent RHJ, Massof C, Kelly AMB, Adam T & Bagshawe K D: A phase—I study of repeated therapy with radiolabelled antibody to carcinoembryonic antigen using intermittent or continuous administration of cyclosporin A to suppress the immune response, Int. J. Cancer 1991; 47; 659–664.
10. Pedley R B, Dale R, Boden J A, Begent R H J, Keep P A Green A J. The effect of second antibody clearance on the distribution and dosimetry of radiolabelled anti-CEA antibody in a human colonic tumour xenograft model. Int. J. Cancer 1989; 43; 713–718.
11. Pedley R B, Boden J A, Boden R, Dale R, Begent R H J. Comparative radioimmunotherapy using intact or F(ab')$_2$ fragments of $^{131}$I anti-CEA antibody in a colonic xenograft model. Br. J. Cancer 1993; 68; 69–73.

12. Ledermann J A, Begent R H J, Bagshawe K D, Riggs S J, Searle F, Glaser M G, Green A J, Dale R G. Repeated antitumour antibody therapy in man with suppression of the host response by Cyclosporin A. Br. J. Cancer 1988; 58; 654.
13. Boxer GM, Begent R H J, Kelly A M B, Southall P J, Blair S B, Theodoron N A, Dawson P M, Ledermann J A. Factors influencing variability of localisation of antibodies to carcinoembryonic antigen (CEA) in patients with colorectal carcinoma—implications for radioimmunotherapy. Br. J. Cancer 1992; 65; 825–831.
14. Winter G and Milstein C. Man-made antibodies. Nature 1991; 349; 293–299.
15. Chester K A, Begent R H J, Robson L, Keep P, Pedley R B, Boden J A, Boxer G, Green A, Winter G, Cochet O, Hawkins R E. Phage libraries for generation of clinically useful antibodies. Lancet February 1994; 343; 455–456.
16. Chester K A, Robson L, Keep P A, Pedley R B, Boden J A, Boxer G M, Hawkins R E, Begent R H J. Production and tumour binding characterisation of a chimeric anti-CEA FAB expressed in Escherichia coli. Int. J. Cancer, 57, 62–72 (1994b).
17. Orlandi R, Gussow D H, Jones P T, Winter G. Cloning immunoglobulin variable domains for expression by the polymerase chain reaction, Proc. nat. Acad. Sci. (Wash.), 86, 3383–3837 (1989).
18. Clackson T, Hoogenboom H R, Griffiths A D, Winter G. Making antibody fragments using phage display libraries. Nature, 352, 624–28 (1991).
19. Hawkins R E, Zhu D, Ovecka M, Winter G, Hamblin T J, Long A, Stevenson F K. Idiotypic vaccination against B-cell lymfoma. Rescue of variable region gene sequences from biopsy material for assembly as single-chain Fv vaccines. Blood, 83, 3279 (1994).
20. Hunter W M, Greenwood F C. Preparation of Iodine-131 labelled human growth hormone of high specific activity. Nature, 194, 495–496 (1962).
21. Pedley R B, Begent R H, Boden J A, Boden R, Adam T, Bagshawe K D. The effect of radiosensitizers on radioimmunotherapy, using $^{133}$I-labelled anti-CEA antibodies in a human colonic xenograft model. Int. J. Cancer, 47, 597–602 (1991).
22. Pak K Y, Nedelman M A, Tam S H, Wilson B, Daddona P E. Labelling and stability of radiolabeled antibody fragments by a direct $^{99m}$Tc-labelling method. Nucl. Med. Biol. 1992; 19:699–677.
23. Huston J S, McCartney J, Tai M S, et al. Medical applications of single-chain antibodies (review). Int. Rev. Immunol. 1993; 10(2–3): 195–217.
24. Skerra A, Plucktun A. Assembly of a functional immunoglobulin fragment in Escherichia coli. Science 1988; 240: 1038–1041.
25. Cochet O, Prospero T, Chester K A, Teilland J-L, Winter G, Hawkins R E. Bivalent and bispecific diabodies for colorectal tumour targeting. Abstract of Keystone Symposium, 7–13 March 1994, Lake Tahoe, Calif. J. Cellular Biochem 1994 518D 211, abstract no. T 508.
26. Waldmann. Monoclonal Antibodies in Diagnosis and Therapy. Science 1991, 252, 1657–1661.
27. Hermentin and Seiler. Investigations with monoclonal antibody drug (anthracycline) conjugates. Behring Inst. Mitt. 1988, 82, 197–215.
28. Hemsley A, Arnheim N, Toney M D, Cortopassi G, Galas D J (1989). A simple method for site-directed mutagenesis using the polyunerase chain reaction. Nucl. Acids Res. 17: 6545–6551.
29. Bagshawe et al. Antibody, Immunoconjugates, and Radiopharmaceuticals (1991), 4, 915–922.
30. Blair S D, Theodorou N A, Begent R H J et al (1990). Comparison of anti-fetal colonic microvillus and anti-CEA antibodies in peroperative radioimmunolocalisation of colorectal cancer, Br. J. Cancer, 61, 891.
31. Tuttle S E, Jewell S D, Mojzisik C M et al (1988). Introperative radioimmunolocalisation of colorectal carcinoma with a hand-held gamma probe and MAb B72.3: comparison of in vivo gamma probe counts with in vitro MAb radiolocalisation. Int. J. Cancer, 42, 352.
32. Begent R H J, Chester K A, Connors T, Crowther D, Fox B, Griffiths E, Hince T A, Lederman J A, McVie J G, Minor P, Secher D S, Schwartsmann G, Thorpe R, Wilbin C, Zwierzina H. (1993) Cancer Research Campaign Operation Manual for control recommendations for products derived from recombinant DNA technology prepared for investigational administration to patients with cancer in phase I trials. Eur. J. Cancer. 29A, 1907.
33. Sulkowski E, (1985). Purification of proteins by IMAC. Trends Biotechnol. 3,1.
34. Keep P A, Leake B A, Rogers G T (1978). Extraction of CEA from tumour tissue, foetal colon and patients sera, and the effect of perchloric acid. Br. J. Cancer, 37, 171.
35. Greenwood F C, Hunter W M (1963). The preparation of $^{133}$I-labelled human growth hormone of high specific radioactivity. Biochem. J. 89, 114.

We claim:

1. An antibody specific for carcinoembryonic antigen (CEA) which has a dissociation constant (Kd) of less than 5.0 nM for said antigen and whose six complementarity determining regions (CDRS) each respectively have the six sequences shown at the following locations in SEQ ID NO: 2: Gly 52 to His 61, Trp 76 to Glu 85, Gly 125 to Tyr 135, Ser 185 to His 194, Ser 210 to Ser 216 and Gln 249 to Thr 257.

2. An antibody specific for CEA which has a Kd of less than 5.0 nM for CEA and has a variable (V) region of the sequence from Gln 27 to Lys 267 of SEQ ID No: 2.

3. An antibody specific for CEA which has a Kd of less than 5.0 nM for CEA and has the sequence set forth in SEQ ID No: 2.

4. An antibody according to claim 1 claims which binds to human colorectal adenocarcinoma but does not bind to the following normal tissues: liver, kidney, tonsil, lung, brain, testis, ovary, cervix, breast, blood films, placenta, spleen, thyroid, oesophagus, stomach, pancreas, lymph node and skeletal muscle.

5. An antibody according to claim 1 which is a single chain Fv (scFv) antibody.

6. An antibody according to claim 1 which is obtainable from a bacteriophage library.

7. An antibody according to claim 1 having an antitumor agent or a detectable label attached thereto.

8. An antibody according to claim 1 having a free Cys residue at or near its N- or C-terminus.

9. An antibody according to claim 8 wherein $^{99m}$Tc is attached to said Cys residue.

10. An antibody according to claim 1 having a His tag of at least three consecutive His residues at or near its N- or C-terminus.

11. An antibody according to claim 7 wherein the antitumor agent is an enzyme which activates a prodrug or is a cytokine.

12. An antibody according to claim 11 wherein said enzyme which activates a prodrug is bacterial carboxypeptidase G2 (CPG2).

13. An antibody according to claim 11 wherein said cytokine is tumour necrosis factor alpha (TNF-α).

14. An antibody according to claim 11 wherein said cytokine is interleukin-2 (IL-2).

15. A bispecific antibody which comprises two variable regions, one of which is the variable region of an antibody as defined in claim 1.

16. A composition comprising an antibody as claimed in claim 7 and a pharmaceutically acceptable carrier or diluent.

17. A method for obtaining a scFv antibody as claimed in claim 5, which method comprises (i) selecting from a bacteriophage library a bacteriophage which expresses said antibody, (ii) infecting a bacterial host cell with the selected bacteriophage, (iii) culturing the host cell under conditions such that said antibody is expressed, and (iv) recovering said antibody from the culture.

18. A method according to claim 17 wherein the bacteriophage library is made by (a) immunizing an animal with CEA, (b) obtaining lymphocytes from the animal, (c) preparing cDNAs encoding antibody VH and VL regions from the mRNA of the lymphocytes, (d) joining VH and VL coding regions by a sequence encoding a linker, and (f) inserting the joined regions into bacteriophage.

19. A method for purifying an antibody comprising a His tag as claimed in claim 10 from a biological liquid, which method comprises (i) contacting a solid support containing metal ions with the biological liquid under conditions such that the antibody binds to the support, (ii) removing biological liquid which is not bound to the support, and (iii) recovering the antibody from the support.

20. A method according to claim 19 wherein the metal ions are $Cu^{2+}$ ions.

21. A method according to claim 19 wherein the solid support is the matrix of an affinity chromatography column.

22. A method for detecting a colorectal tumour in a patient, which method comprises (i) administering to the patient an antibody as claimed in claim 1 having a detectable label attached thereto, and (ii) detecting the label, wherein detection of the label allows detection of the tumor.

23. An antibody specific for CEA which has a Kd of less than 5.0 nM for CEA and has a variable heavy (VH) chain region of the sequence from Gln 27 to Ser 146 of SEQ ID No:2 and a variable light (VL) chain region of the sequence from Glu 162 to Lys 267 of SEQ ID No:2.

* * * * *

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 810 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 1:

```
GAG  ACA  GTC  ATA  ATG  AAA  TAC  CTA  TTG  CCT  ACG  GCA  GCC  GCT  GGA  TTG         4 8
Glu  Thr  Val  Ile  Met  Lys  Tyr  Leu  Leu  Pro  Thr  Ala  Ala  Ala  Gly  Leu
 1             5                      1 0                      1 5
```

| | | | | | | | | | | | | | | | | |
|---|---|---|---|---|---|---|---|---|---|---|---|---|---|---|---|---|
| TTA | TTA | CTC | GCG | GCC | CAG | CCG | GCC | ATG | GCC | CAG | GTG | AAA | CTG | CAG | CAG | 96 |
| Leu | Leu | Leu | Ala | Ala | Gln | Pro | Ala | Met | Ala | Gln | Val | Lys | Leu | Gln | Gln | |
| | | 20 | | | | | 25 | | | | | 30 | | | | |
| TCT | GGG | GCA | GAA | CTT | GTG | AGG | TCA | GGG | ACC | TCA | GTC | AAG | TTG | TCC | TGC | 144 |
| Ser | Gly | Ala | Glu | Leu | Val | Arg | Ser | Gly | Thr | Ser | Val | Lys | Leu | Ser | Cys | |
| | | 35 | | | | | 40 | | | | | 45 | | | | |
| ACA | GCT | TCT | GGC | TTC | AAC | ATT | AAA | GAC | TCC | TAT | ATG | CAC | TGG | TTG | AGG | 192 |
| Thr | Ala | Ser | Gly | Phe | Asn | Ile | Lys | Asp | Ser | Tyr | Met | His | Trp | Leu | Arg | |
| | 50 | | | | | 55 | | | | | 60 | | | | | |
| CAG | GGG | CCT | GAA | CAG | GGC | CTG | GAG | TGG | ATT | GGA | TGG | ATT | GAT | CCT | GAG | 240 |
| Gln | Gly | Pro | Glu | Gln | Gly | Leu | Glu | Trp | Ile | Gly | Trp | Ile | Asp | Pro | Glu | |
| 65 | | | | | 70 | | | | | 75 | | | | | 80 | |
| AAT | GGT | GAT | ACT | GAA | TAT | GCC | CCG | AAG | TTC | CAG | GGC | AAG | GCC | ACT | TTT | 288 |
| Asn | Gly | Asp | Thr | Glu | Tyr | Ala | Pro | Lys | Phe | Gln | Gly | Lys | Ala | Thr | Phe | |
| | | | | 85 | | | | | 90 | | | | | 95 | | |
| ACT | ACA | GAC | ACA | TCC | TCC | AAC | ACA | GCC | TAC | CTG | CAG | CTC | AGC | AGC | CTG | 336 |
| Thr | Thr | Asp | Thr | Ser | Ser | Asn | Thr | Ala | Tyr | Leu | Gln | Leu | Ser | Ser | Leu | |
| | | | 100 | | | | | 105 | | | | | 110 | | | |
| ACA | TCT | GAG | GAC | ACT | GCC | GTC | TAT | TAT | TGT | AAT | GAG | GGG | ACT | CCG | ACT | 384 |
| Thr | Ser | Glu | Asp | Thr | Ala | Val | Tyr | Tyr | Cys | Asn | Glu | Gly | Thr | Pro | Thr | |
| | | 115 | | | | | 120 | | | | | 125 | | | | |
| GGG | CCG | TAC | TAC | TTT | GAC | TAC | TGG | GGC | CAA | GGG | ACC | ACG | GTC | ACC | GTC | 432 |
| Gly | Pro | Tyr | Tyr | Phe | Asp | Tyr | Trp | Gly | Gln | Gly | Thr | Thr | Val | Thr | Val | |
| | 130 | | | | | 135 | | | | | 140 | | | | | |
| TCC | TCA | GGT | GGA | GGC | GGT | TCA | GGC | GGA | GGT | GGC | TCT | GGC | GGT | GGC | GGA | 480 |
| Ser | Ser | Gly | Gly | Gly | Gly | Ser | Gly | Gly | Gly | Gly | Ser | Gly | Gly | Gly | Gly | |
| 145 | | | | | 150 | | | | | 155 | | | | | 160 | |
| TCA | GAA | AAT | GTG | CTC | ACC | CAG | TCT | CCA | GCA | ATC | ATG | TCT | GCA | TCT | CCA | 528 |
| Ser | Glu | Asn | Val | Leu | Thr | Gln | Ser | Pro | Ala | Ile | Met | Ser | Ala | Ser | Pro | |
| | | | | 165 | | | | | 170 | | | | | 175 | | |
| GGG | GAG | AAG | GTC | ACC | ATA | ACC | TGC | AGT | GCC | AGC | TCA | AGT | GTA | AGT | TAC | 576 |
| Gly | Glu | Lys | Val | Thr | Ile | Thr | Cys | Ser | Ala | Ser | Ser | Ser | Val | Ser | Tyr | |
| | | | 180 | | | | | 185 | | | | | 190 | | | |
| ATG | CAC | TGG | TTC | CAG | CAG | AAG | CCA | GGC | ACT | TCT | CCC | AAA | CTC | TGG | ATT | 624 |
| Met | His | Trp | Phe | Gln | Gln | Lys | Pro | Gly | Thr | Ser | Pro | Lys | Leu | Trp | Ile | |
| | | 195 | | | | | 200 | | | | | 205 | | | | |
| TAT | AGC | ACA | TCC | AAC | CTG | GCT | TCT | GGA | GTC | CCT | GCT | CGC | TTC | AGT | GGC | 672 |
| Tyr | Ser | Thr | Ser | Asn | Leu | Ala | Ser | Gly | Val | Pro | Ala | Arg | Phe | Ser | Gly | |
| | 210 | | | | | 215 | | | | | 220 | | | | | |
| AGT | GGA | TCT | GGG | ACC | TCT | TAC | TCT | CTC | ACA | ATC | AGC | CGA | ATG | GAG | GCT | 720 |
| Ser | Gly | Ser | Gly | Thr | Ser | Tyr | Ser | Leu | Thr | Ile | Ser | Arg | Met | Glu | Ala | |
| 225 | | | | | 230 | | | | | 235 | | | | | 240 | |
| GAA | GAT | GCT | GCC | ACT | TAT | TAC | TGC | CAG | CAA | AGG | AGT | AGT | TAC | CCA | CTC | 768 |
| Glu | Asp | Ala | Ala | Thr | Tyr | Tyr | Cys | Gln | Gln | Arg | Ser | Ser | Tyr | Pro | Leu | |
| | | | | 245 | | | | | 250 | | | | | 255 | | |
| ACG | TTC | GGT | GCT | GGC | ACC | AAG | CTG | GAG | CTG | AAA | CGG | GCG | GCC | | | 810 |
| Thr | Phe | Gly | Ala | Gly | Thr | Lys | Leu | Glu | Leu | Lys | Arg | Ala | Ala | | | |
| | | | 260 | | | | | 265 | | | | | 270 | | | |

( 2 ) INFORMATION FOR SEQ ID NO: 2:

( i ) SEQUENCE CHARACTERISTICS:
        ( A ) LENGTH: 270 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

| | | | | | | | | | | | | | | | |
|---|---|---|---|---|---|---|---|---|---|---|---|---|---|---|---|
| Glu | Thr | Val | Ile | Met | Lys | Tyr | Leu | Leu | Pro | Thr | Ala | Ala | Ala | Gly | Leu |
| 1 | | | | 5 | | | | | 10 | | | | | 15 | |
| Leu | Leu | Leu | Ala | Ala | Gln | Pro | Ala | Met | Ala | Gln | Val | Lys | Leu | Gln | Gln |

|   |   |   |   |   | 20 |   |   |   |   | 25 |   |   |   |   | 30 |   |   |
|---|---|---|---|---|----|---|---|---|---|----|---|---|---|---|----|---|---|
| Ser | Gly | Ala<br>35 | Glu | Leu | Val | Arg | Ser | Gly<br>40 | Thr | Ser | Val | Lys<br>45 | Leu | Ser | Cys |
| Thr | Ala<br>50 | Ser | Gly | Phe | Asn<br>55 | Ile | Lys | Asp | Ser | Tyr | Met<br>60 | His | Trp | Leu | Arg |
| Gln<br>65 | Gly | Pro | Glu | Gln | Gly<br>70 | Leu | Glu | Trp | Ile | Gly<br>75 | Trp | Ile | Asp | Pro | Glu<br>80 |
| Asn | Gly | Asp | Thr | Glu<br>85 | Tyr | Ala | Pro | Lys | Phe<br>90 | Gln | Gly | Lys | Ala | Thr<br>95 | Phe |
| Thr | Thr | Asp | Thr<br>100 | Ser | Ser | Asn | Thr | Ala<br>105 | Tyr | Leu | Gln | Leu | Ser<br>110 | Ser | Leu |
| Thr | Ser | Glu | Asp<br>115 | Thr | Ala | Val | Tyr<br>120 | Tyr | Cys | Asn | Glu | Gly<br>125 | Thr | Pro | Thr |
| Gly | Pro<br>130 | Tyr | Tyr | Phe | Asp | Tyr<br>135 | Trp | Gly | Gln | Gly | Thr<br>140 | Thr | Val | Thr | Val |
| Ser<br>145 | Ser | Gly | Gly | Gly | Gly<br>150 | Ser | Gly | Gly | Gly | Gly<br>155 | Ser | Gly | Gly | Gly | Gly<br>160 |
| Ser | Glu | Asn | Val | Leu<br>165 | Thr | Gln | Ser | Pro | Ala<br>170 | Ile | Met | Ser | Ala | Ser<br>175 | Pro |
| Gly | Glu | Lys | Val<br>180 | Thr | Ile | Thr | Cys | Ser<br>185 | Ala | Ser | Ser | Ser | Val<br>190 | Ser | Tyr |
| Met | His | Trp<br>195 | Phe | Gln | Gln | Lys | Pro<br>200 | Gly | Thr | Ser | Pro | Lys<br>205 | Leu | Trp | Ile |
| Tyr | Ser<br>210 | Thr | Ser | Asn | Leu | Ala<br>215 | Ser | Gly | Val | Pro | Ala<br>220 | Arg | Phe | Ser | Gly |
| Ser<br>225 | Gly | Ser | Gly | Thr | Ser<br>230 | Tyr | Ser | Leu | Thr | Ile<br>235 | Ser | Arg | Met | Glu | Ala<br>240 |
| Glu | Asp | Ala | Ala | Thr<br>245 | Tyr | Tyr | Cys | Gln | Gln<br>250 | Arg | Ser | Ser | Tyr | Pro<br>255 | Leu |
| Thr | Phe | Gly | Ala<br>260 | Gly | Thr | Lys | Leu | Glu<br>265 | Leu | Lys | Arg | Ala | Ala<br>270 |   |   |

( 2 ) INFORMATION FOR SEQ ID NO: 3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 3:

TGGTGATGAC ATGCGGCCGC CCGTTTGAT        29

( 2 ) INFORMATION FOR SEQ ID NO: 4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 4:

TCATCACTAA TAAGAATTCA CTGGCCG        27

( 2 ) INFORMATION FOR SEQ ID NO: 5:

-continued ( i ) SEQUENCE CHARACTERISTICS:
  ( A ) LENGTH: 183 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO: 5:

```
AAGCTTGCAT GCAAATTCTA TTTCAAGGAG ACAGTCATA ATG AAA TAC CTA TTG        54
                                            Met Lys Tyr Leu Leu
                                                            275

CCT ACG GCA GCC GCT GGA TTG TTA TTA CTC GCG GCC CAG CCG GCC ATG       102
Pro Thr Ala Ala Ala Gly Leu Leu Leu Leu Ala Ala Gln Pro Ala Met
            280                     285                     290

GCC CAG GTG CAG CTG CAG GTC GGC CTC GAG ATC AAA CGG GCG GCC GCA       150
Ala Gln Val Gln Leu Gln Val Gly Leu Glu Ile Lys Arg Ala Ala Ala
            295                     300                     305

TGT CAT CAC CAT CAT CAC CAT TAATAAGAAT TC                             183
Cys His His His His His His
            310
```

( 2 ) INFORMATION FOR SEQ ID NO: 6:

( i ) SEQUENCE CHARACTERISTICS:
    ( A ) LENGTH: 44 amino acids
    ( B ) TYPE: amino acid
    ( D ) TOPOLOGY: linear ( i i ) MOLECULE TYPE: protein ( x i ) SEQUENCE DESCRIPTION: SEQ ID NO: 6:

```
Met Lys Tyr Leu Leu Pro Thr Ala Ala Ala Gly Leu Leu Leu Leu Ala
 1               5                  10                  15

Ala Gln Pro Ala Met Ala Gln Val Gln Leu Gln Val Gly Leu Glu Ile
            20                  25                  30

Lys Arg Ala Ala Ala Cys His His His His His His
            35                  40
```

( 2 ) INFORMATION FOR SEQ ID NO: 7:

( i ) SEQUENCE CHARACTERISTICS:
    ( A ) LENGTH: 24 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO: 7:

```
CAT CAC CAT CAT CAC CAT TAA TAA                                        24
His His His His His His
            48
```

( 2 ) INFORMATION FOR SEQ ID NO: 8:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: protein ( x i ) SEQUENCE DESCRIPTION: SEQ ID NO: 8:

```
His His His His His His
 1               5
```